United States Patent [19]
Kosak et al.

[11] Patent Number: 5,643,764
[45] Date of Patent: *Jul. 1, 1997

[54] REACTIONS USING HEAT-RELEASABLE REAGENTS IN WAX BEADS

[76] Inventors: Kenneth M. Kosak; Matthew K. Kosak, both of 3194 S. 4400 West, West Valley City, Utah 84120

[*] Notice: The term of this patent shall not extend beyond the expiration date of Pat. No. 5,413,924.

[21] Appl. No.: 396,257

[22] Filed: Mar. 1, 1995

Related U.S. Application Data

[63] Continuation-in-part of Ser. No. 936,357, Aug. 27, 1992, Pat. No. 5,413,924, which is a continuation-in-part of Ser. No. 835,758, Feb. 13, 1992, abandoned.

[51] Int. Cl.$^6$ .......................... C12P 19/34; C12N 11/04; C12N 15/00; G01N 33/544
[52] U.S. Cl. .................... 435/91.1; 435/6; 435/7.1; 435/41; 435/89; 435/91.4; 435/91.41; 435/174; 435/177; 435/182; 436/528; 436/535; 530/812; 530/817; 935/16; 935/33
[58] Field of Search ............................ 435/41, 174, 177, 435/182, 6, 7.1, 89, 91.4, 91.41; 436/528, 535; 530/812, 817; 935/16, 33

[56] References Cited

U.S. PATENT DOCUMENTS

| | | | |
|---|---|---|---|
| 4,235,671 | 11/1980 | Papahadjopoulos et al. | 424/19 |
| 4,303,717 | 12/1981 | Andrews | 428/200 |
| 4,384,835 | 5/1983 | Bland | 425/7 |
| 4,607,050 | 8/1986 | Kieran et al. | 514/520 |
| 4,743,548 | 5/1988 | Crossway et al. | 435/172.3 |
| 4,749,620 | 6/1988 | Rha et al. | 428/402.2 |
| 4,900,556 | 2/1990 | Wheatley et al. | 424/450 |
| 5,000,955 | 3/1991 | Gould et al. | 424/409 |
| 5,093,130 | 3/1992 | Fujii et al. | 424/463 |
| 5,106,633 | 4/1992 | Edens et al. | 476/8 |
| 5,114,854 | 5/1992 | Bertholdt | 435/240.1 |
| 5,200,236 | 4/1993 | Lang et al. | 427/213 |
| 5,413,924 | 5/1995 | Kosak et al. | 435/177 |

FOREIGN PATENT DOCUMENTS

| | | |
|---|---|---|
| 2627404 | 8/1989 | France . |
| WO91/12342 | 8/1991 | WIPO . |
| WO91/18110 | 11/1991 | WIPO . |

OTHER PUBLICATIONS

G. Ruano et al., "Heat–Soaked PCR: An Efficient Method for DNA Amplification with Applications to Forensic Analysis", *BioTechniques*, pp. 266–274, vol. 13, No. 2 (1992).

M.L. Jozwiakowski et al., "Characterization of a Hot–Melt Fluid Bed Coating Process for Fine Granules", *Pharmaceutical Research*, vol. 7, No. 11, pp. 1119–1126 (1990).

R. Nir et al., "Single–Cell Entrapment and Microcolony Development within Uniform Microspheres Amenable to Flow Cytometry", *Applied and Environmental Microbiology*, vol. 56, No. 9, pp. 2870–2875 (Sep. 1990).

J.H. Fendler, "Polymerized Surfactant Vesicles: Novel Membrane Mimetic Systems", *Science*, vol. 223, pp. 888–894 (Mar. 1984).

Larsson et al., "Alcohol Production by Magnetic Immobolized Yeast", *Biotechnology Letters*, pp. 501–506 (1979).

Cayper et al., Prog. Colloid Polym. Scie., vol. 82, pp. 353–359 (1990).

*Primary Examiner*—David M. Naff
*Attorney, Agent, or Firm*—Madson & Metcalf

[57] ABSTRACT

A reagent such as a heat resistant enzyme is entrapped in a material such as wax or a liposome that releases the reagent when heated so the reagent is available for reaction. In a preferred embodiment, wax beads containing the reagent are prepared by injecting the reagent into beads of molten wax and cooling to solidify the wax. In another embodiment, droplets of a solution of the reagent are dropped through a layer of molten wax to coat the droplets with the wax and the coated droplets are cooled to solidify the wax. The entrapped reagents have application in nucleic acid hybridizations, polymerase chain reactions (PCR), reverse transcriptase reactions (RTR), nucleic acid sequencing, and product generating reactions such as colorimetic, fluorometric and chemiluminescent enzyme labeled immunoassays.

28 Claims, 5 Drawing Sheets

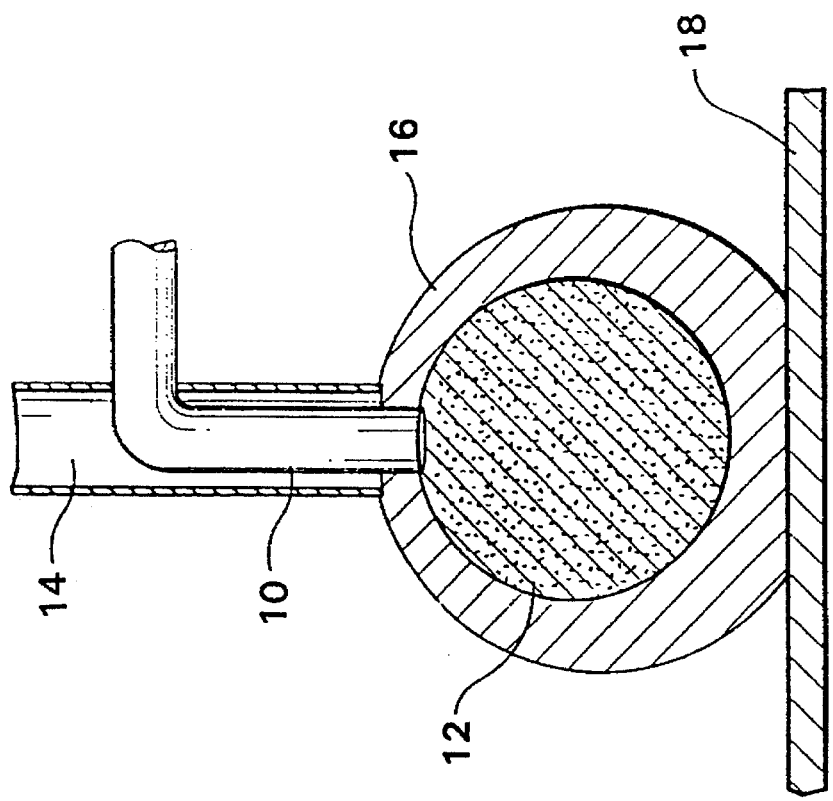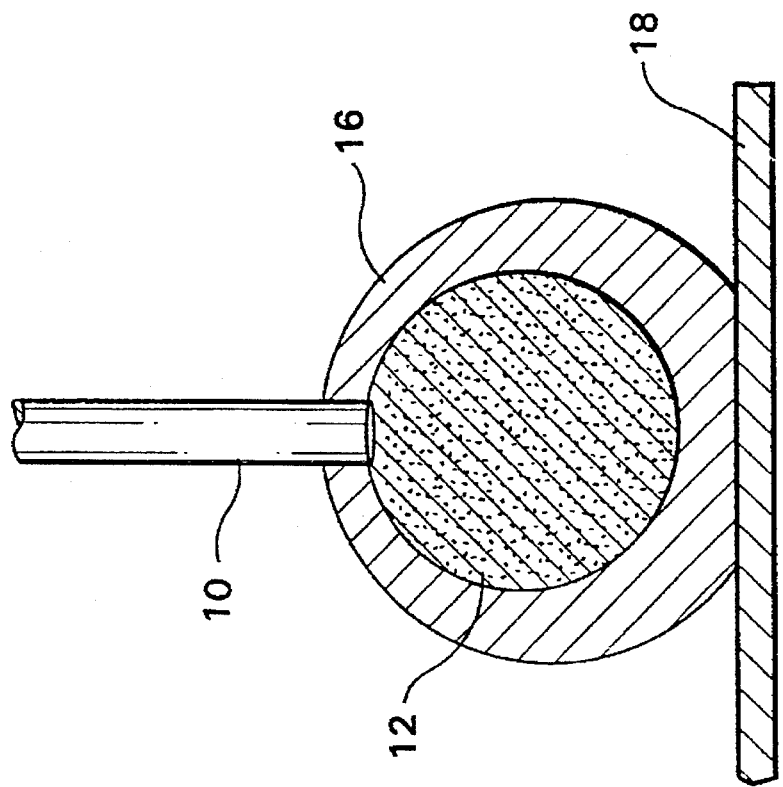

5,643,764

1

REACTIONS USING HEAT-RELEASABLE REAGENTS IN WAX BEADS

RELATED PATENT APPLICATIONS

This application is a continuation-in-part of U.S. patent application Ser. No. 07/936,357, filed Aug. 27, 1992, now U.S. Pat. No. 5,413,924, which is a continuation-in-part of U.S. patent application Ser. No. 07/835,758, filed Feb. 13, 1992, now abandoned.

FIELD OF THE INVENTION

This invention relates to the preparation and use of reagents that are entrapped in various particulate compositions, especially wax beads, and subsequently released by heating for use in various in vitro chemical, biochemical and immunological reactions.

DESCRIPTION OF THE BACKGROUND ART

A variety of chemical reactions are improved through the addition of heat. Increased temperature is of particular importance in certain biochemical reactions such as nucleic acid hybridizations where heat is frequently used to increase the specificity of the binding reaction. Elevated temperatures (i.e., greater than 70° C.), are also useful in overcoming problems of secondary RNA structures in the reverse transcriptase reaction (RTR), used to produce complementary DNA (cDNA) from RNA (*Biochemistry* 30, 7661–7666, 1991). Elevated temperatures (i.e., greater than 70° C.), are also useful in DNA sequencing procedures.

Heat is being employed in nucleic acid amplification such as the polymerase chain reaction (PCR). The PCR (U.S. Pat. Nos. 4,683,202 and 4,683,195) employs a heating and cooling cycle to drive the reaction. First, the reaction mixture is heated to, or above, the nucleic acid melting temperature (denaturization), then cooled to allow specific oligonucleotide primers to bind to the sample (annealing), and then heated to optimize the addition of complementary bases to the amplified nucleic acid (extension). Using heat stable, Taq DNA polymerase (U.S. Pat. No. 4,889,818), this cycle of denaturing, annealing and extension is repeated as many times as needed to generate the desired product.

The PCR is quickly becoming a major tool in molecular biology, and the need for high specificity during amplification is an increasing problem.

One method suggested for increasing the PCR specificity is called "booster" PCR (see application section below), where initial amplification is done with diluted amounts of primer, that are subsequently increased or "boosted" for later cycles.

Another method for increasing specificity is pre-amplification heating. This method has been described by H. A. Erlich, et al., *Science* 252, 1643–1651 (1991), and R. T. D'Aquila, et al., *Nucleic Acids Res.* 19, 3749 (1991). It requires exclusion of at least one essential reagent (dNTP's, $Mg^{2-}$, DNA polymerase or primers), from the reaction until it has been heated to the desired annealing temperature. However, the procedure requires the sample tubes to be closed while heating, and reopened for addition of the missing reagent.

The procedure, also called Hot-Start PCR by Perkin Elmer Cetus, Conn., has been improved by the use of a wax barrier formed in the reaction tube that separates some of the reagents until the tube is heated to melt the barrier.

Perkin Elmer Cetus now sells a wax pellet (Ampliwax™) for this purpose. Their published procedure includes the following steps: (1) to a sample tube containing primers, $Mg^{2-}$, dNTP's in buffer, add one pellet of Ampliwax™; (2) heat the tube to 80° C. to melt the wax; (3) cool to room temperature to form a wax barrier on top of the solution; (4) over the wax barrier, add the sample with DNA polymerase in buffer; and (5) start normal PCR cycling.

The problems with this method are: (1) it is limited to open tubes and is not readily used in other containers such as sealed capillaries or the tubular containers described in the inventor's Disclosure Document No. 291836 (this disclosure relates to tubing with constantly heated or cooled zones where PCR is done by moving a liquid sample between the zones to heat and cool it); (2) there is potential for error in forming each wax barrier in each tube; and (3) the melting and cooling of wax adds additional steps to the PCR method.

The uses for Ampliwax™ wax pellets and greases to form barriers between reagents in a reaction tube are more fully disclosed in international publication number WO 91/12342, international patent application number PCT/US91/01039, to Cetus Corporation (hereinafter referred to as the "Cetus application").

The Cetus application is directed to the use of wax or grease as a substitute for oil in forming a vapor barrier over aqueous samples in a PCR reaction tube. Wax or grease is cast as a molten layer over an aqueous solution and allowed to cool and solidify. This layer can also be used as a barrier between subsets of PCR reagents within the reaction tube.

On page 8 of the Cetus application, there is a suggestion for PCR reagents "wherein one subset is incorporated into a lighter-than-water oil, grease, or wax which is layered on top of any aqueous suspension or solution." This is referring to oil, grease or wax that is layered over an aqueous solution to form a barrier in the reaction tube. At page 26, the Cetus application teaches that a wax or grease pellet added to an aqueous solution in a PCR tube is heated to melt the wax and form a barrier over the aqueous solution.

The Cetus application suggests that oil solubility and water extraction are potential obstacles of incorporating PCR reagents in wax or grease. Apparently, these problems arise because a hydrophobic barrier layer is needed to separate aqueous reagents within a PCR reaction tube. Low oil solubility can be a problem for reagents suspended in grease or wax. The Cetus application suggests using a water-wax or water-grease emulsion to incorporate PCR reagents in wax or grease. Only one reagent, magnesium salts of fatty acids, is disclosed as being suitable for incorporation into wax or grease in the absence of emulsification. At page 25, the Cetus application teaches that the molten layer of grease or wax must be cast and solidified quickly before the reagent is extracted into the aqueous layer below. To minimize extraction during casting of the barrier layer, the Cetus application recommends using "wax or grease with the lowest practical melting point, preferably in the range of about 40°–50° C."

It will be appreciated that there is a need in the art for methods of performing the PCR as well as in other high temperature methods such as reverse transcriptase and nucleic acid hybridizations, which are not limited to open tubes and which do not require the additional steps of forming a wax barrier in each tube.

SUMMARY OF THE INVENTION

This invention is directed toward the use of wax beads or particles that contain a heat-releasable reagent. The heat-releasable reagent is preferably in an aqueous suspension entrapped within the wax beads. The reagent entrapped within wax beads solves the problems of adding stepwise, one or more essential reagents into a reaction medium when needed, without reopening containers or interrupting the procedure.

This invention comprises compositions and methods for preparation and in vitro use of mobile or particulate, entrapped reagents that do not react until heated to a minimal temperature. When heated to the predetermined temperature, the reagents are released into the surrounding medium such as a solution, and become available for reaction with other substances in the medium. The most preferred applications for this invention are in various types of nucleic acid hybridizations, PCR's, RTR's, nucleic acid sequencing and product generating reactions such as colorimetric, fluorometric and chemiluminescent enzyme labeled immunoassays.

The composition has the following advantages:

(1) A reaction mixture in a solution or some other medium can be prepared that is complete with all of the necessary reagents in place and one or more of the key reagents or substances is suitably entrapped in a heat-releasable, mobile composition. Then, the reaction mixture may be held indefinitely and no reaction will occur until the medium is heated to a predetermined temperature.

(2) Several identical or different complete reaction mixtures can be prepared and stored as needed, and eventually all reactions can be initiated simultaneously. This will avoid the problem of adjusting for product differences in time-sensitive and/or kinetic reactions such as enzymatic production of colored, fluorescent or chemiluminescent products used in immunoassays and molecular biology. Also, by using appropriate inhibitors and/or blocking agents as entrapped reagents, all reactions can be stopped simultaneously when the mixture is heated to release the reagent.

(3) Entrapment of certain reagents will afford protection from degradation during storage.

(4) Some entrapped reagents are more easily and/or accurately dispensed.

(5) The process step of preparing molten wax or grease barriers is eliminated.

(6) Suitable reagents are not limited to those which are soluble in wax, but include any reagent in an aqueous suspension.

(7) The use of high melting temperature wax beads permits the PCR or other high temperature reactions to be optimized.

Figure 1:
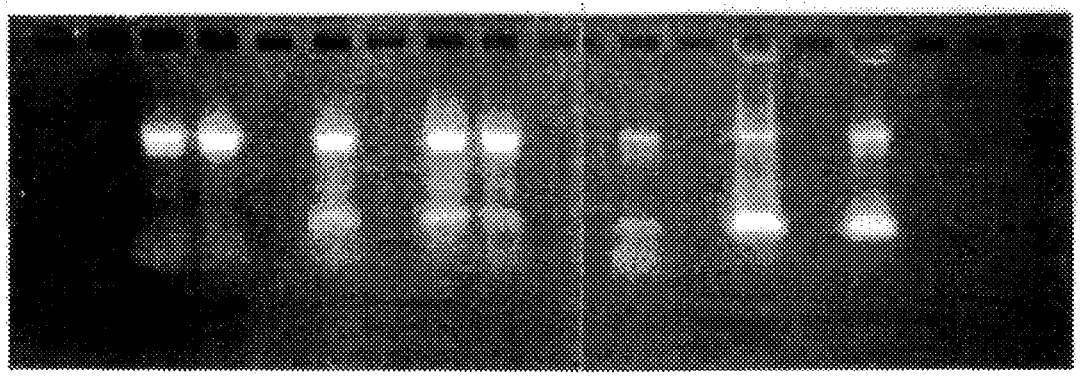
FIG. 1 illustrates a photograph of a 2% agarose gel, ethidium bromide stained and visualized over ultraviolet light. This photograph demonstrates PCR products in the upper band of each lane, corresponding to 500 base pair fragments of amplified Lambda DNA.

Lanes A and B show PCR products using Taq polymerase entrapped in paraffin wax and subsequently heat-released to perform the reaction. (See Example I.)

Lane C shows a PCR product using the same starting solution as in A and B except Taq polymerase was added directly into the solution as a control. (See Example I.)

Lanes D and E show PCR products using dNTP's entrapped in paraffin wax and subsequently heat-released to perform the reaction. (See Example II.)

Lane F shows PCR a product using dNTP's entrapped in beeswax and subsequently heat-released to perform the reaction. (See Example III.)

Lanes G and H show PCR products using Taq polymerase entrapped in liposomes and also added directly into the solution. (See Example IV.)

FIG. 2 is a cross-sectional diagram showing a bead of molten waxy polymer 16, formed on a flat surface 18, after injection of heat-releasable reagent 12, before the injector tube 10 has been removed.

FIG. 3 is a cross-sectional diagram showing a molten bead formed on a flat surface 18, by dispensing molten waxy polymer 16 from a heated dispenser tube 14. The diagram also shows an injector tube 10 leading through, and concentric with, the heated dispenser tube. Injection of heat-releasable reagent 12, has just been completed, before the tubing assembly is removed.

Figure 4:
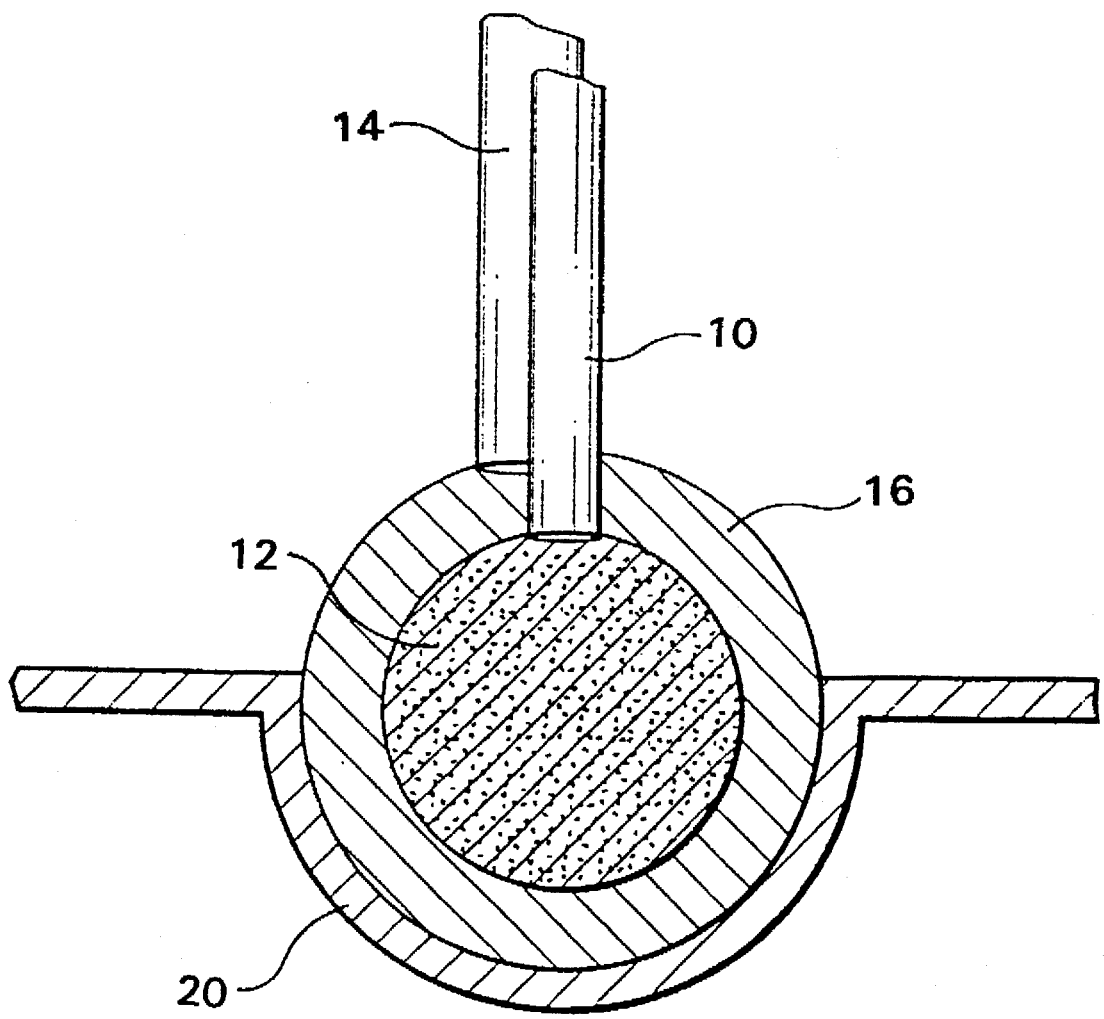

FIG. 4 is a cross-sectional diagram showing a molten bead formed in a cup or mold 20, by dispensing molten waxy polymer 16 from a heated dispenser tube 14. The diagram also shows an injector tube 10 in parallel and in contact with, the heated dispenser tube. Injection of heat-releasable reagent 12, has just been completed, before the tubing assembly is removed.

Figure 5:
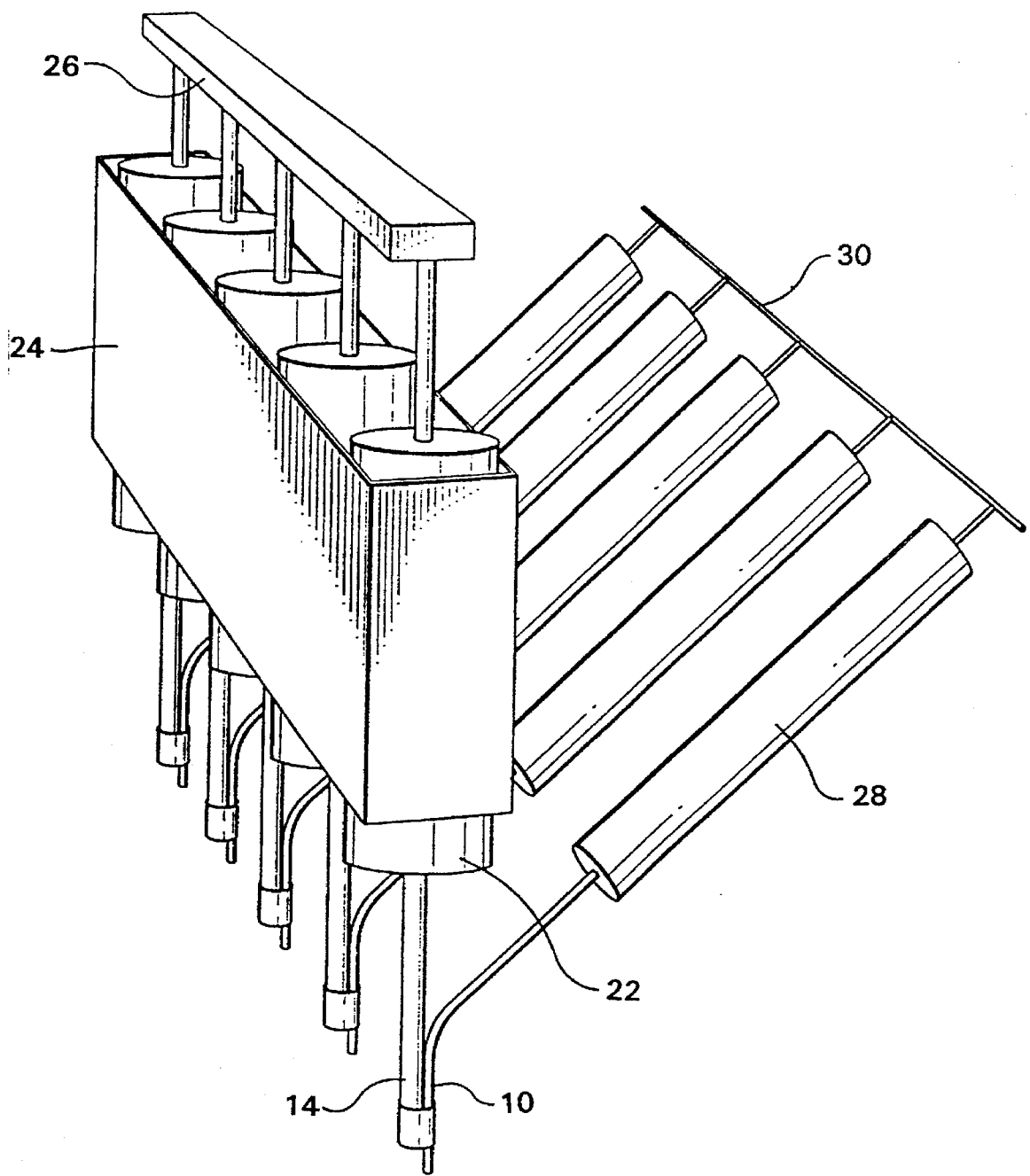

FIG. 5 is a diagram of a device for multiple dispensing of molten waxy polymer beads and injecting them with heat-releasable reagent. The molten waxy polymer is contained in syringes 22, that are heated by heating element 24. When the dispenser plungers 26, are pushed down, melted waxy polymer beads are extruded from the dispenser tubes 14. Then, heat-releasable reagent is injected through injector tubes 10, from injector syringes 28, by pushing on injector plungers 30.

Figure 6:
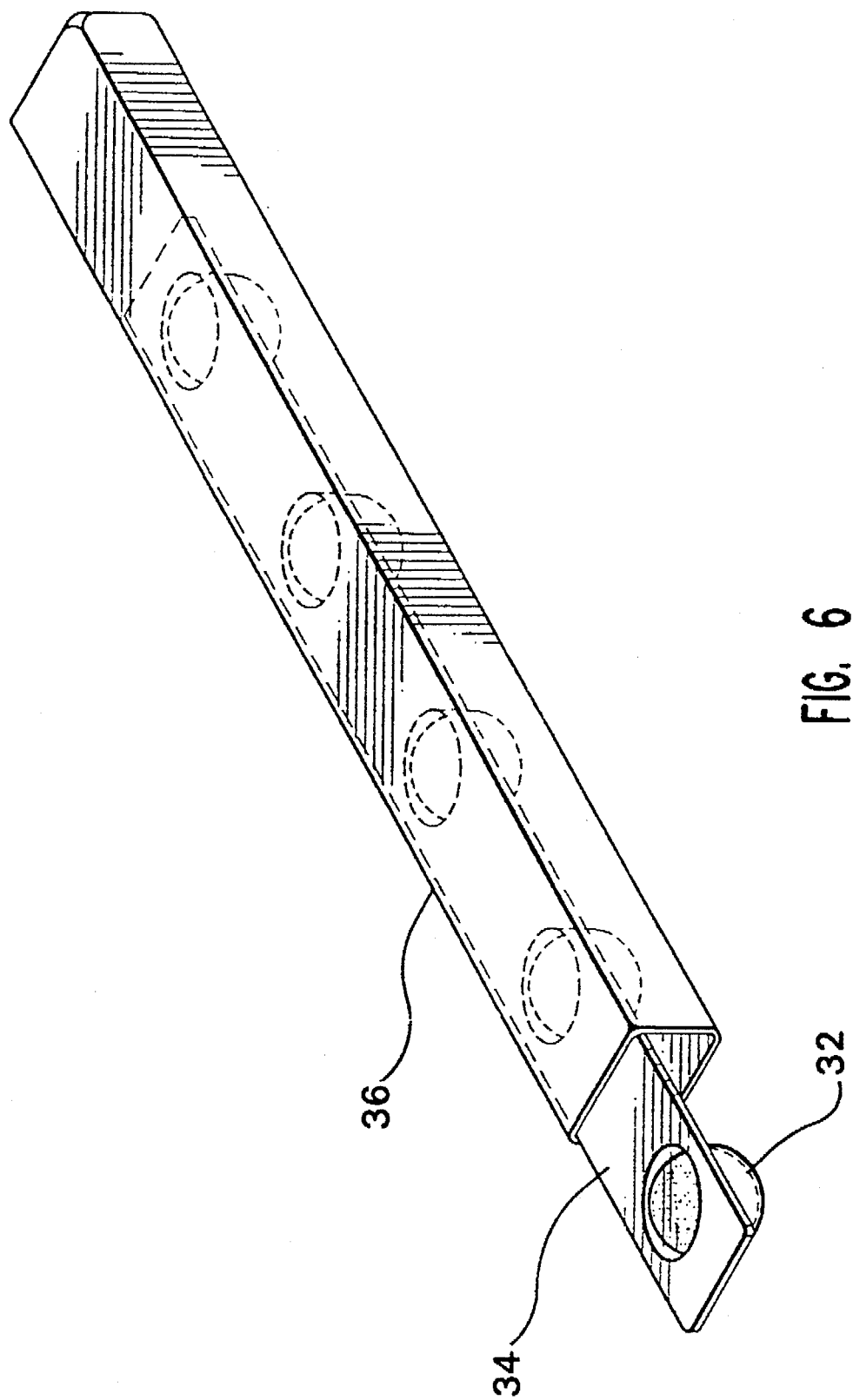

FIG. 6 shows an arrangement that combines molding, packaging and subsequent dispensing of injected beads. Injected beads 32) have been formed directly in a plastic strip of molds 34 and then covered by slipping a plastic sleeve 36 over the beads in the molds.

DETAILED DESCRIPTION OF THE PREFERRED EMBODIMENTS

For the purposes of this invention, the following definitions are used.

Entrapment.

Entrapment means enclosing a substance within an entrapping material to form a barrier between the outside medium and the entrapped substance.

Heat-Releasable.

Heat-releasable means that the entrapping material is for in vitro use and is essentially inert with the surrounding medium but can be melted, dissolved, lysed or dispersed when exposed to the desired critical temperature. Preferred critical temperatures are above room temperature especially above 30° C., the upper limit depending on the heat tolerance of the reagents used and the type of reaction employed. Goods results have been obtained with entrapping material which melts at temperatures greater than 50° C. and preferably greater than 60° C. The entrapping material is water resistant or water insoluble and is not readily dissolved with acids, bases, enzymes, antibodies or lytic agents. Therefore, there is little or no dissolution and release of the entrapped substance when held in an aqueous medium below the critical temperature. This definition is meant to exclude the majority of entrapping materials presently used for many drug delivery systems.

Dispensable Body.

A dispensable body is defined as an entrapment composition that is in a mobile, particulate form (particulate entrapment), that can be readily dispersed or dispensed into a medium. Depending on the desired application, the size of the dispensable body may vary. When the dispensable body is formed as a small particle (i.e., less than one, to hundreds of microns in diameter), such as a granule, microcapsule, vesicle, liposome, artificial cell, filament, flake or fragment, it can be dispensed as a suspension, emulsion, colloid or slurry in a liquid medium or it can be dispensed as a free-flowing powder. When the dispensable body is formed as a larger particle (i.e., greater than one millimeter diameter) it can be dispensed as a bead, pellet or capsule, or a coarse powder or slurry.

Entrapped Reagents.

An entrapped reagent is defined as any suitable substance that can be entrapped in a heat-releasable material and subsequently heated without excessive inactivation for release into a reaction.

(a). Heat Resistant Enzymes:

For the purposes of this invention, a heat resistant enzyme is defined as any enzyme that retains most of its activity after one hour at 40° C. under optimal conditions. Many such enzymes can be used such as those from thermophilic organisms. For example, various RNA polymerases such as Q beta replicase from bacteriophage, among others, and DNA polymerases from *Thermophilus sp.* ("Taq"), *Thermoccocus sp.* ("vent"), *Thermus sp.* ("Tth" and recombinant "rTth"), and *Pyroccocus sp.* ("pfu"), as well as DNA ligases such as "ampligase", from Epicentre Technologies, and any other enzymes from thermophilic microorganisms and invertebrates, including forms produced by recombinant DNA technology. Other enzymes that can be used are reverse transcriptases, restriction endonucleases, kinases, proteases, nucleases, RNAses, DNAses, phosphatases (i.e., alkaline phosphatases "AP"), peroxidases (i.e., horseradish peroxidase "HRP") and many others. Preferably these enzymes have sufficient thermal stable properties naturally (i.e., by isolation from thermophilic organisms), or by suitable chemical modification, or by genetic engineering.

(b). Enzyme Substrates:

Another useful group of reagents for entrapment in heat-releasable reagents is any suitable substrate. For example, in the PCR, these include any labeled or unlabeled nucleotides and nucleoside triphosphates (NTP's), any deoxynucleoside triphosphates (dNTP's), any dideoxynucleoside triphosphates (ddNTP's) and ribonucleoside triphosphates. Some examples are: 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 2'-deoxyuridine 5'-triphosphate (dUTP), 2'-deoxyinosine 5'-triphosphate (dITP), 7-deaza-2'-deoxyguanosine 5'-triphosphate (I-$N^7$-dGTP), among others. Also included are members of this group labeled with radioactive nuclides such as $^3$H, $^{14}$C, $^{32}$P, $^{35}$S, and $^{125}$I, among others.

Also included are various derivatives, analogs and labeled forms of NTP's, dNTP's and ddNTP's, such as biotin labeled, bio-4-dUTP, and bio-11-dUTP, also dNTP's labeled with digoxigenin (DIG-UTP, DIG-dUTP, DIG-ddUTP, *Biotechniques*, 12, 104–113 (1992)), sulfur, cyclodextrins, fluorophores, isotopes, and amino groups such as 5-(3-aminoallyl)-2'-deoxyuridine 5'-triphosphate (AA-dUTP).

(c). Phosphorylated Substrates:

Other substrates include any phosphorylated substrate that produces a colored, fluorescent or chemiluminescent product when dephosphorylated, as with AP, such as 5-bromo-4-chloro-3-indoyl phosphate (BCIP) and nitro blue tetrazolium (NBT); 4-methylumbelliferyl phosphate, and any phosphorylated dioxetanes (3-(2'-spiroadamantanane)-4-methoxy-4-(3"phosphoryloxy)phenyl-1,2-dioxetane (AMPPD)) and HMPPD, among others.

(d). Oxidase Substrates:

Also included are any substrates for peroxidases such as o-phenylenediamine (OPD), 3,3'-diaminobenzidine tetrahydrochloride dihydrate (DAB), and 3,3',5,5'-tetramethylbenzidine (TMB), among others.

(e). Metal Salts:

Also included are various salts (i.e., chlorides or sulfates), of metals such as Mg, Mn, Fe, Co, Cu, Zn, etc.

(f). Oligonucleotides:

Another useful group of entrapped reagents includes any suitable RNA, DNA, and labeled or unlabeled oligonucleotides for use as hybridization probes or primers. For instance, in the PCR, any appropriate antisense (reverse) primers and sense (forward) primers can be used including those labeled with any suitable label such as biotin, AP, digoxigenin, sulfur, cyclodextrins, fluorophores, isotopes, and proteins. Also included are members of this group labeled with radioactive nuclides such as $^3$H, $_{14}$C, $^{32}$P, $^{35}$S, and $^{125}$I, among others.

(g). Inhibitors and Chelators:

Another useful group of entrapped reagents are any enzyme inhibitors or poisons. Also included are various chelating agents such as ethylenediaminetetraacetic acid (EDTA), ethylene glycol-bis(beta-aminoethyl ether)N,N,N', N'-tetraacetic acid (EGTA), and 2,2',2",2"'-(1,2-ethanediylidene-tetrakis[thio])tetrakisacetic acid (ETTA), 1,2-bis(2-aminophenoxy)ethane-N,N,N',N'-tetraacetic acid (BAPTA), among others.

(h). Antibodies:

Another useful group of entrapped reagents are any antibodies, antibody fractions or monoclonal antibodies, including derivatives thereof.

(i). Antigens:

Also included are any antigens, or derivatives thereof.

(j). Avidins and Streptavidins:

Also included are any avidins an streptavidins including derivatives, labeled forms, fractions and recombinant DNA products.

(k). Biotins:

Also included are any biotins, aminobiotins, photobiotins and any biotinylated proteins, nucleic acids, carbohydrates, etc.

(l). Labeling substances:

Also included are various labeling materials such as any isothiocyanate compounds (FITC, etc.), sulfonyl chloride compounds (4,7-bis(chlorosulfophenyl)-1,10-phenanthroline-2,9-dicarboxylic acid (BCPDA)), N-hydroxysuccinimide esters (N-hydroxysuccinimidobiotin), nucleic acid intercalating dyes (ethidium bromide, psoralens and psoralen derivatives, etc.).

The most preferred intercalating dyes are ethidium bromides, oxazole orange and thiazole orange, especially their dimers (i.e., YOYO and TOTO, Molecular Probes Inc.), trimers and various derivatives. Also included are any suitable dyes and fluorophores conjugated to and/or as inclusion complexes with cyclodextrins and any of the cyclodextrin derivatives disclosed in disclosure documents #247302, Mar. 12, 1990; #244763, Feb. 6, 1990; and #248131, Mar. 19, 1990. These dyes and fluorophores, including YOYO and TOTO, can be subsequently detected by fluorescence, or by a chemiluminescent reaction such as energy transfer from decomposition of certain 1,2 dioxetanes, or peroxyoxylates.

Heat-Releasable Liposome.

A liposome is a rounded, submicron to many micron-sized, liquid-filled vesicle composed of a lipid bilayer membrane that completely encloses an aqueous space. The lipid bilayer may form a single membrane (unilamellar) or may form several concentric membranes (multilamellar) around the aqueous space. The membrane may be impermeable or semipermeable depending on composition. Liposomes may be synthesized from single chain lipids or surfactant polymers, for example, see: Fendler, J., Science 223, 888-894 (1984); Hammes, G. G. et al., Biochemistry 9, 2555-2563 (1970), among others. They are generally made from mixtures of phospholipids, sterols and various amphophilic lipids. A variety of proteins, enzymes, substrates, polyamino acids, nucleotides, oligonucleotides, antibodies, antigens and various reaction components can be entrapped within the membrane structure which makes certain liposomes a highly versatile tool for research and analytical applications. Also, the membrane composition can be modified through the incorporation of dyes, chromophores and magnetic substances. The properties of temperature stability, fluidity, permeability and surface charge can be altered with sterols, antibiotics and charged or uncharged lipids. The liposomal membrane can also be modified by cross-linking integral lipids or surfactants, or by incorporating into the membrane a wide variety of lipids, proteins, lipoproteins and glycolipids with "activated" functional groups or with specific ligands coupled thereto. For this invention, liposomes with thermal stability in the range of 30-100 degrees centigrade and with a narrow (i.e., 1-5 degrees) transition (melting) temperature range, are preferred. Such thermal stability can be achieved by using natural or synthetic phospholipids, lipids, lecithins, surfactants, etc., that have aliphatic carbon chains of 14 or more carbons.

Many of the methods used for preparing liposomes in the prior art would be useful for preparing the liposomes of this invention. The major modifications would involve the inclusion of the desired substrate(s) or enzyme such as peroxidases, alkaline phosphatases, DNA polymerases, ligases and Q beta replicase, that is preferably heat stable, in the interior of the liposome. For examples of synthesis methods that would be useful, see: Antanavage, J. et al., Biophy. J. 21, 122a (1978); Ashcroft, R. G. et al., Biochim. Biophys. Acta 643, 191-204 (1981); Ashcroft, R. G. et al., Biochim. Biophy. Acta 730, 231-238, (1983); Deamer, D. et al., Biochim. Biophys. Acta 443, 629-634 (1976); Guo, L. S. S. et al., J. Lipid Res. 21, 993-1003 (1980); Haxby, J. A. et al., Proc. Natl. Acad. Sci. USA 64, 290-295 (1969); Kinsky, S. C. et al., Biochemistry 8, 4149-4158 (1969); Kitagawa, T. et al., Nature 254, 254-256 (1975); Reeves, J. P. et al., J. Cell. Physiol. 73, 49-60 (1968); Szoka, F. C. et al., Proc. Natl. Acad. Sci. USA 75, 4194-4198 (1978); Szoka, F. Jr., Annu. Rev. Biophys. Bioeng. 9, 467-508 (1980); Taguchi, T., Biochim. Biophys. Acta 729, 229-236 (1983); Takashi, T. et al., J. Biochem. 87, 679-685 (1980); Uemura, K. et al., Biochemistry 11, 4085-4094 (1972); Uemura, K. et al., J. Immunol. Methods 53, 221-232 (1982); Van Rooijen, N. et al., Cellular Immmunol. 49, 402-407 (1980); Weissmann, G. et al., J. Clinical Invest. 53, 536-543 (1974); Weissmann, G. et al., Proc. Nat. Acad. Sci. USA 72, 88-92 (1975); Wreschner, D. H. et al., Biochem. Soc. Trans. 6, 930-933 (1978); Leaver, J. et al., Biochim. Biophys. Acta 732, 210 (1983); Mowri, H., et al., J. Biochem. 95, 551 (1984); Mueller, P., et al., Biophys, J. 44, 375 (1983); Neitchev, V. Z., Intern. J. Biochem. 16, 235 (1984); Chapman, U.S. Pat. No. 4,348,329; and MacDonald, R. I., et al., in: Liposome Letters, A. D. Bangham, ed., Acad. Press, N.Y. (1983), among others.

New Liposome Properties for Heat-Release Reactions.

Various materials may be incorporated into the liposome compositions disclosed to impart additional properties and thereby improve their usefulness in certain applications, especially for all of the various types of RTR, PCR and ligase chain reactions. For instance, the addition of suitably coated, ferrous or magnetic particles in the loading solution may be used to give the liposomes magnetic properties (Ithakissios, D. S., Clin. Chim. Acta 84(1-2), 69-84, 1978). This may be useful for various manipulations such as dispensing, transferring, washing, separating or lysing the liposomes as desired before or during a thermocycling reaction. Magnetic materials may also serve to increase mixing by magnetic stirring of the solution.

Also, the liposome membrane may be modified by polymerizing or cross-linking certain membrane lipids or dialkyl surfactants containing vinyl, methacrylate, diacetylene, isocyano or styrene coupling groups by chemical means or with ultraviolet light. The degree of cross-linking could be controlled to give the desired stability against premature lysis of, or leakage from the liposome. For more on materials and methods that are applicable to synthesizing polymerized liposome tracers, this invention, see previously cited: J. H. Fendler, Science 223, 888-894 (1984); J. Leaver, et al., Biochim. Biophys. Acta 732, 210-218 (1983); "Polymers as Aids in Organic Chemistry", N. K. Mathur, et al., eds., Academic Press, N.Y. (1980).

Another method for stabilizing the liposomes of this invention would be to use the polymerization methods of P. S. Ash, et al., U.S. Pat. No. 4,448,765. To prepare the polymerized liposome of this invention one would include the appropriate amount of aliphatic lipophilic polymers as disclosed by Ash et al. as part of the vesicle membrane to obtain the desired degree of heat stability.

Another significant improvement would be to render the liposomes resistant to damage by dehydration for storage. This may be possible by using membrane stabilizers such as the disaccharide, trehalose (Crowe, J. H. et al., Science 219, 1177-1183 (1983)). For example, liposomes could be synthesized with dipalmitoyl phosphatidylcholine or other suitable lipids, included in the lipid membrane. Then, these liposomes could be dehydrated in the presence of 20% or more concentration of trehalose.

Coupling or Cross-Linking Aqents: A coupling or crosslinking agent is defined here as a substance or energy, such as ultraviolet light, that produces active functional groups on an entrapment material or dispensable body such as a liposome, gel particle, artificial cell, microcapsule, or waxy polymer. Depending on the functional group on the entrapment material, the appropriate coupling agent is used to activate the functional group or react with it. When the coupling agent is a substance, it may provide the linkage between the lipids, phospholipids proteins, carbohydrates or surfactants in the entrapment material. Examples of coupling agents are glutaraldehyde, formaldehyde, cyanogen bromide, azides, p-benzoquinone, succinic anhydrides, carbodiimides, maleimides, epichlorohydrin, periodic acid, ethyl chloroformate, dipyridyl disulfide, polyaldehydes, dimethylsuberimidate and other forms of bis(imidoesters), as well as certain heterobifunctional reagents such as m-maleimidobenzoyl-N-hydroxysuccinimide, N-succinimidyl-3-(2-pyridyldithio)-proprionate and N-succinimidyl(4-iodoacetyl)aminobenzoate, among others.

Liposome Entrapped Reagents. To obtain the greatest signal per liposome, it is desirable to have liposomes with maximal amounts of entrapped reagent such as DNA polymerase, (for the PCR) or ligase (for ligase chain reaction) and/or oligonucleotide primer, or dNTP's or other enzymes and substrates. This can be accomplished through using large, single membrane (unilamellar), vesicles. However, multilamellar vesicles may be preferred.

Several established methods are available for liposome synthesis. These include methods that employ spontaneous swelling, sonication, ether vaporization, detergent dialysis, reverse-phase evaporation and salting-out. The reagents, etc. can be entrapped inside the liposomes during their synthesis. Most reagents are available from Sigma Chemical Co., Mo., or Avanti Polar Lipids, Ala., or can be synthesized. A suitable method can be adapted from the methods in the literature, including; Papahadjopoulos, D., R. Fraley and T. Heath, "Optimization of Liposomes as a Carrier for the Intracellular Delivery of Drugs and Macromolecules", *Liposomes and Immunobiology*, p. 151–164, Tom/Six eds., Elsevier N. Holland, Inc. (1980), and; Szoka Jr., F., and D. Papahadjopoulos, "Procedure for Preparation of Liposomes with Large Internal Aqueous Space and High Capture by Reverse-Phase Evaporation," *Proc. Natl. Acad. Sci. USA* 75, 4194–4198 (1978), and many others.

Heat-Releasable Wax or Waxy Polymer.

Wax or wax-like polymers are water insoluble materials that are solid or semi-solid at room temperature, but can be melted above room temperature to form a dispersible liquid. Waxy polymers include any naturally occurring and synthetic waxes, and wax esters that have the desired melting temperature and are suitably inert for use in the reaction.

Examples of suitable waxes and greases are esters of various long-chain (fatty) alcohols and long-chain acids, preferably where at least one member of the ester has 10 or more carbon atoms, including various unsaturated and branched chain types and also those esters of glycerols and sterols.

Also, certain free alcohols or acids with even or odd numbers of carbons, have wax-like properties of melting temperature and inertness, and would be suitable as heat-releasable waxy polymers. Some examples of saturated fatty acids (and approximate melting point), that can be used in this invention are; capric (31.3° C.), lauric (48° C.), myristic (58° C.), palmitic (63°–64° C.), margaric (59.3° C.), stearic (70.5°–71.5° C.), arachidic (76°–77° C.), behenic (81°–82° C.), tetracosanic (84.5°–85.5°C.), lignoceric (75°–80° C.), cerotic (78° C.), melissic (91° C.), among others. Some examples of unsaturated fatty acids (and approximate melting point), that can be used in this invention are; tiglic (64°–65° C.), hypogaeic (33°–49° C.), gaidic (39° C.), physetoleic (30° C.), elaidic (44°–45° C.), oleic (58°–59° C.), isooleic (44°–45° C.), erudic (33°–34° C.), brassidic (65° C.), isoerudic (54°–56° C.), among others.

Some examples of fatty alcohols (and approximate melting point), that can be used in this invention are; octadecyl (59° C.), carnaubyl (68°–69° C.), ceryl (80° C.), melissyl (88° C.), phytol, among others. Also included are various esters of these and other fatty acids with any suitable fatty alcohols, or sterols such as cholesterol, or glycerols.

Other examples are natural or suitably modified or derivatized waxes such as various plant derived waxes, including carnauba wax, ouricuri wax, candelilla wax, raphia wax, apple, cotton and cactus waxes; waxes produced by bacteria (i.e., cetyl stearate); fungi, protozoa and algae; various invertebrate waxes including insect waxes such as beeswaxes (i.e., triacontyl palmitate, palmatyl palmitate), and *Coccus sp.* derived waxes (i.e., lac, cochineal and Chinese insect).

Also included are various derivatives, extracts, and combinations of these materials. For instance, any oil that is suitably hydrogenated, or various new combinations of long-chain fatty acids and long-chain alcohols, usually of 12 or more carbon atoms, to form new esters together and/or in combination with glycerols or sterols. Also included are various waxes produced by recombinant DNA technology.

Most preferred waxes or waxy polymers are many natural or synthetic long chain hydrocarbons such as white waxes, paraffins, silicon waxes, polychlorinated or polyfluorinated hydrocarbons, polyether waxes and polyester waxes.

Some examples of paraffins and approximate melting point (m.p.), that can be used in this invention are; hexacosane (56.4° C.), hentriacosane (59° C.), octacosane (61.4° C.), nonacosane (62.7° C.), triacontane (65.6° C.), hentriacontane (67.6° C.), dotriacontane (69.5° C.), tetratriacontane (72.5° C.), pentatriacontane (74.4° C.), hexatriacontane (75.7° C.), including others with shorter or longer carbon chains.

One suitable source of paraffin waxes for use in this invention are those from Fluka Chemical Corp., St. Louis, Mo., with m.p.'s of; 44°–46° C., 50°–52° C., 54°–56° C., 58°–60° C., and 68°–74° C. It has been found that use of high melting temperature wax provides better results in the PCR procedure. The wax melting temperature is preferably greater than 50° C. and most preferably greater than 60° C.

Depending on the desired properties, such as melting point, inertness, solubility, buoyancy, etc., any of the waxy polymers described here can be combined in various proportions to give the desired result. Useful waxy polymers can also include any suitable long-chain hydrocarbon or ester mentioned previously that has been suitably derivatized to give it neutral buoyancy in an aqueous medium. For example, a long-chain hydrocarbon or ester can be suitably chlorinated or fluorinated to make it less buoyant.

Other types of polymers that can be combined with waxy polymers are polyethylenes, polypropylenes, certain gums and rubbers. Examples are various kinds of latex, gutta-percha, balata, chicle and various derivatives. Also included are synthetic rubbers such as isoprene polymers, hydrogenated rubber, butadiene polymers, chloroprene polymers and butyl polymers.

Also, suitably coated, ferrous or magnetic particles can be included in any waxy polymer to give the particles magnetic properties.

Also, under suitable conditions, the waxy polymer can have coloring added to it in the form of a colored or fluorescent dye, preferably any suitable oil or fat soluble dye can be used. Some examples are, Sudan III, Sudan IV, and Sudan Black B.

Heat-Releasable Gel.

A heat-releasable gel is any suitable gelling material that will form a matrix for entrapping reagents that can subsequently be melted to release the reagents when heated to a critical temperature. Examples of such gels are; agars, agaroses, carageenans, cellulose derivatives, gelatins, and alginates. Also included are suitable combinations of these gels and/or mixed with other polymers such as acrylamides, polyethylenes, styrenes, proteins, gums, latexes and resins.

PREPARATION METHODS FOR HEAT-RELEASABLE REAGENTS

A. Heat-Releasable Liposome Preparations

A variety of saturated and unsaturated lipids and phospholipids can be used to prepare heat-releasable liposomes.

Some examples are egg and soybean lecithins, dilauroylphosphatidyl choline (DLPC), dimyristoylphosphatidyl choline (DMPC), dipalmitoylphosphatidyl choline (DPPC), distearoylphosphatidyl choline (DSPC), dibehenoylphosphatidyl choline (DBPC), diarachidoylphosphatidyl choline (DAPC), any synthetic phospholipids with even or odd numbered, saturated or unsaturated carbon chains and their combinations, lipid esters, fatty acids, cholesterol, ceramides, cerebrosides, gangliosides, as well as derivatives with diacetylenic groups for subsequent polymerization, etc.

In one example, a lipid mixture is prepared composed of DLPC dissolved in a 1:1 ethyl ether:chloroform solvent. The concentration of total lipids can be 70–100 micromoles per ml of solvent. In mixtures of more than one lipid, the molar ratios of the lipids themselves may be varied to obtain the most suitable results.

A loading solution is prepared composed of a concentrated (0.5% or more) solution of reagent to be entrapped (i.e., enzyme or substrate) in 0.01M suitable buffer, pH 6–8. In addition, other substances such as proteins (bovine serum albumin (BSA)), sucrose, glucose, Ficoll, polyvinylpyrrolidones, polyethylene glycols, etc., may be included. To a 50 ml evaporation flask, is added 3 ml of the lipid mixture and 1 ml of the loading solution. The solution is sonicated to produce a homogeneous dispersion. The solvent phase is then evaporated off at a suitable temperature, while rotating at approximately 200 rpm under reduced pressure, using a water powered aspirator pump. Residual solvent is quickly removed by gel column chromatography using Sepharose 4B. The column is equilibrated with 0.01M suitable buffer containing 0.15M NaCl, pH 7–8, or if membrane extrusion is used, the column is equilibrated with the loading solution.

Or, suitable liposomes can be made by overlaying the loading solution over a dried layer of the desired lipid formulation in a glass dish, and allowing them to form spontaneously at a suitable temperature.

Membrane extrusion can be used to improve size uniformity of the liposomes. Typically, this involves transferring the liposome suspension to a syringe in an excess of the original loading solution. The suspension is then forced through a narrow gauge needle or through a controlled-pore, polycarbonate membrane of 0.45–0.8 micron pore size, (Nuclepore, Calif.). Untrapped reagent is removed by passing the liposomes through a Sepharose 4B column equilibrated with buffer. The suspension can be concentrated by dialysis against polyethylene glycol or by centrifugation, and stored in buffer.

B. Heat-Releasable Waxy Matrix Preparations

One or more reagents to be entrapped are mixed directly with the melted wax or waxy polymer. Depending on the application, the reagent can be in granular, powder or liquid form, or previously dissolved or suspended in a suitable liquid. Mixing is done by stirring, extruding or sonicating the reagent and waxy polymer together. If soluble, the reagent may dissolve into the waxy polymer, or it may form a suspension of particles or liquid droplets or a colloid.

In any case, the melted mixture is then extruded or sprayed into particles or beads for use in subsequent reactions. Several suitable methods can be used, with appropriate modifications, such as spray congealing as described by A. G. Cusimano, et al., *J. Pharmaceutical Sci.*, 57, 1104–1112 (1968), and W. R. Marshall, Jr., *Chem. Engin. Prog. Monogr. Series* 50, No. 2, Amer. Inst. Chem. Engin., New York, N.Y. (1954), among others. Basically, the method is to spray the melted mixture through a heated orifice of appropriate diameter to produce atomization, and air cool the resulting droplets so that they congeal in the air. The conditions of temperature, pressure and waxy polymer used are adjusted to ensure suitable concentration and activity of entrapped reagent upon release. It may be desirable to use a vibrating nozzle similar to that described by R. Nir, et al., *Appl. Environ. Microb.*, 56, 2870–2875 (1990), to produce more uniform microspheres of entrapped reagent.

Or, the mixture is extruded to form filaments or sheets that are subsequently chopped, crushed, or ground into smaller particles.

C. Heat-Releasable Waxy Coating Preparations

One or more reagents to be coated are prepared in small granules either as pure reagent or mixed with a suitable carrier substance such as a carbohydrate (i.e., glucose, sucrose, ficoll), or any suitable gel or gel bead (i.e., agarose), protein (i.e., albumin) or polymer (i.e., polyethylene glycol, acrylamide, styrene). The granules are then coated with a layer of any suitable waxy polymer using various methods such as the "hot melt fluid bed coating process" described by M. J. Jozwiakowski, et al., in *Pharmaceutical Res.*, 7, 1119–1126 (1990).

For instance, the granules are fluidized in a chamber using an upward flow of warm air, and the waxy polymer is melted and sprayed into the chamber as the granules are recirculated and suitably coated.

In another method, the granules are coated by simply mixing with the melted waxy polymer. The mixture is then sprayed into a collection chamber or extruded into a cooling medium (i.e., water) to form coated granules or droplets. Or, the mixture is extruded to form filaments or sheets that are subsequently chopped, crushed, or ground into smaller particles.

Another method suitable for solid particles or liquid droplets of heat-releasable reagent, is to drop the droplets through one or more moving sheets of molten waxy polymer. The sheet of waxy polymer is prepared as a continuous stream ejected under pressure from a nozzle flattened to give the desired shape. As the particles or droplets fall through the sheet of molten waxy polymer, they are coated. They are allowed to continue falling through a long enough cooling zone, such as refrigerated tower, until the waxy polymer coating has solidified. Then they are collected at the bottom on a gentle, cushioned slope to prevent damage from the fall.

PREFERRED METHOD FOR A WAXY COATING

A preferred method of the instant invention for entrapping liquid heat-releasable reagents in a waxy coating is an "injected bead" method, where the desired liquid reagent is injected into a bead of molten waxy polymer, which is then allowed to cool and solidify. It has been discovered that the molten waxy polymer bead can be formed and carefully injected on a flat surface to produce liquid heat-releasable reagent coated with a waxy polymer (see Example VI).

However, it is advantageous to form the molten bead in a small cup-like depression or mold. When the waxy polymer is dispensed into such a mold, it produces a molten bead with a curved bottom. The curvature in contact with the molten bead has the advantage of cooling the bottom into a curved form that tends to keep the injected liquid centered within the waxy polymer as it solidifies. Therefore, less care is needed when injecting the liquid heat-releasable reagent into the bead, which results in a higher percentage of suitable beads (see Example VII).

Plastic molds of various sizes to fit the desired size of injected bead, can be made from any suitable plastic, resin or polymer including acetals, polyallomers, polycarbonates, polyurethanes, polyvinyls, polyethylenes, polypropylenes, styrenes, nylons, acrylics, rubbers, polychlorinated or polyfluorinated polymers and tetrafluoroethylenes.

In addition, plastic molds of suitable thickness and flexibility have the advantage of providing a protective container bottom that can be subsequently covered for storage and/or shipping of the beads. For instance, FIG. 6 is an example of such an arrangement where injected beads 32 have been formed directly in a plastic strip of molds 34 and then covered by slipping a snug fitting plastic sleeve 36 over the beads in the molds. The mold and/or sleeve material can also be composed of suitably stiff, coated paper.

Another advantage is realized by making the molds at specific distances apart to coincide with specific reaction tube or well formats used commercially in various biochemical and enzymatic assays such as ELISA's, and the PCR. For example, molds such as that shown in FIG. 6, would be made at 9 mm center spacing and in strips of 4, 8 or 12, so that they are compatible in spacing with the conventional 96 well microtiter plate format. Or, an entire plate format of 96molds at 9 mm center spacing can be used.

These features make the use of molds for injected beads very advantageous for selling the beads in mercantile kits. For example, beads would be formed directly in suitable polyvinyl or polystyrene molds where the above described strips or plates are covered with a plastic sheet or slipped into a suitable plastic sleeve to form packages which would minimize handling. Plastic molds would also be useful in dispensing the beads by removing the cover on individual beads or from an entire strip or plate and simply dumping out, or pushing the beads out of a flexible mold from the back over each well or tube. If rigid molding is used, then small holes could be made in the bottoms of each well to allow the beads to be pushed out mechanically or by air pressure.

The injected bead method, with or without using molds, is readily adapted to automated or semi-automated methods. For instance, a series of dispensing devices for the molten waxy polymer (i.e., heated syringes and tubing), can be arranged to dispense a row of several molten beads simultaneously. The molten beads can then be injected with heat-releasable reagent by a corresponding row of injecting devices (syringes). After injection, the beads are moved out of the way for a new set of beads to be made. All of the necessary steps can be automated or semi-automated. For instance, precision drivers such as electronically controlled step motors can be used to turn screws that push syringe plungers to dispense the molten waxy polymer and inject the heat-releasable reagent.

Preferably, the heated tube from the waxy polymer dispenser and the tube from the heat-releasable reagent injector lead to the same point. This way, the tip of the injector tube is also heated and is in the proper position to inject right after the molten waxy polymer bead is dispensed. The dispenser and injector tips can be fastened together in parallel, or the injector tip can be suitably threaded a short distance inside the end of the dispenser tube to give concentric tubes.

D. Heat-Releasable Gel Matrix Preparations

One or more reagents to be entrapped are mixed directly with the melted gel. The melted mixture is then extruded or sprayed into particles or beads for use in subsequent reactions. Several suitable methods can be used, with appropriate modifications, such as spray congealing as described previously for waxy polymers.

Or, the melted gel with reagent can be extruded into a cooling medium (i.e., water or oil) to form granules, microbeads or droplets.

A preferred method is to use a gel matrix preparation in the drop bead or injected bead method. For instance, beads, microbeads, or droplets of solidified gel (i.e., 0.2–1% low m.p. agarose), are prepared containing heat-releasable reagent and suitable amounts of other additives such as sucrose, Ficoll or BSA to increased density as needed. Then, the gel beads are dropped through a molten layer of waxy polymer to form "drop beads" as described herein. The resulting product is a gel bead with a waxy polymer coating that can be melted to release the reagents inside.

Or, a suitable mixture of melted gel and heat-releasable reagents can be injected into molten waxy polymer beads as described in Examples VI or VII.

E. Mercantile Kits for Heat-Releasable Preparations

A mercantile kit is defined as a collection of materials such as containers (such as in FIG. 6), reagents, buffer solutions, instructions for use, packaging, and the like, prepared as a package for sale. Any of the heat-releasable reagents disclosed in the instant invention can readily be incorporated into a mercantile kit.

The following applications illustrate the great diversity of uses for the instant invention. With suitable modification by one skilled in the art, the heat-releasable reagents of this invention can be applied to any of the following applications.

Application A.

pCR Using Heat-Releasable DNA Polymerase Reagent.

The DNA sample to be amplified is in a final volume of 0.02–0.1 ml containing; 0.5 mM each of dATP, dCTP, dGTP, and dTTP (or any other suitable labeled or unlabeled dNTP's), 0.002 mM each of any appropriate antisense (reverse) primers and sense (forward) primers, in a buffer of 2.5 mM $MgCl_2$, 500 mM KCl, 100 mM Tris-HCl, 0.1% w/v gelatin, pH 8.3.

Also included is any heat stable DNA polymerase entrapped as a heat-releasable reagent as described previously. In this case, approximately 1 unit of Taq DNA polymerase entrapped in waxy polymer particles or in liposomes that melt at a specific temperature (preferred range 50°–100° C.), is added. The PCR reaction is initiated when the heat-releasable DNA polymerase reagent is melted to release the polymerase into solution.

Amplification is performed by sequential immersion in water baths or in any suitable thermal cycling machine. A "hot start" method is initiated when the sample is heated to the critical releasing temperature of the heat-releasable reagent. Samples are optionally denatured at 98° C. for 30 seconds followed by 20–40 cycles of: 94° C. for 20–60 seconds, 65° C. for 20–60 seconds, 72° C. for 60–120 seconds.

Application B.

pCR Using Heat-Releasable Substrate Reagent.

This example is similar to the method using heat-releasable DNA polymerase reagent except that another reagent is entrapped for heat release besides or instead of the enzyme.

In this case, the appropriate dNTP's entrapped in waxy polymer particles or in liposomes that melt at a specific temperature (preferred range 50°–100° C.), are added instead of dNTP's free in solution. The PCR reaction is initiated when the heat-releasable dNTP reagent is melted to release them into solution.

Or, some dNTP's can be in the solution initially, while certain others, such as any labeled dNTP's are entrapped for release after the desired number of cycles. This is done by having the labeled dNTP's in a high melting point heat-releasable reagent such as 95°–100° C. The initial cycles of PCR are kept below that melting point. When they are needed in the reaction, the temperature is raised to release them.

Application C.
High Temperature RTR.

The instant invention is useful in high temperature reverse transcriptase reactions such those reported by A. L. Schaffer, et al., *Anal. Biochem.* 190, 292–296 (1990) and T. W. Myers, et al., *Biochem.* 30, 7661–7666 (1991). The procedure is modified in that one or more essential reagents, such as Taq DNA polymerase, or Tth DNA polymerase, or dNTP's, are first entrapped in a heat-releasable reagent that melts at or near the desired reaction temperature (i.e., 70° C.). Then, the reaction will not be initiated until it has reached the desired temperature and the reagent(s) are released. The high temperature RTR is reported to improve product specificity and destabilize many secondary structures in the template RNA, to allow more complete transcription.

Application D.
High Temperature Nucleic Acid Sequencing.

This method is based on the procedures of F. Sanger, et al., *Proc. Natl. Acad. Sci. USA* 74, 5463–5467 (1977), S. Tabor, et al., *Proc. Natl. Acad. Sci. USA* 84, 4767–4771 (1987) and M. A. Innis, et al., *Proc. Natl. Acad. Sci. USA* 85, 9436–9440 (1988). This method utilizes the three basic steps of annealing, labeling and extension/termination used in previous dideoxynucleotide methods (Sanger) except that the need for reopening and transferring of reaction products is reduced. For instance, the annealing and labeling reactions can be combined by preparing the template DNA in a mixture with the needed primer(s), Taq DNA polymerase and labeling mixture of dNTP's. However, before addition, the Taq and dNTP's are first entrapped in a heat-releasable reagent that melts at 80°–95° C. Then, the entrapped reagents are not available until the template has been fully denatured (i.e., 80°–95° C.).

Application E.
Coupled High Temperature RTR and PCR.

It has been reported by T. W. Myers, et al., *Biochem.* 30, 7661–7666 (1991) and W. T. Tse, et al., *Gene* 88, 293–296 (1990), that the reverse transcription reaction to make cDNA from RNA and the polymerase chain reaction to amplify the cDNA, can be coupled. The heat-releasable reagents of this invention are useful in reducing the steps normally required. For example, all of the necessary reagents for running the coupled RTR/PCR reaction of Myers, using Tth polymerase, can be combined in a single tube. The modification is that the required amounts of EGTA, $MgCl_2$ and the forward and reverse PCR primers are entrapped in heat-releasable reagents (together or separately), that melt the desired temperature (i.e., 80°–95° C.).

The RTR reaction is run at 70° C. under the required conditions in a thermocycling machine. Then, without the reaction container, the PCR is initiated by raising the temperature to melt and release the entrapped reagents. The required cycle parameters are then used to complete the PCR.

Application F.
Booster PCR With or Without Hot-Start.

This application is based on the methods of G. Ruano, et al., *Nucleic Acids Res.* 17, 5407 (1989), and G. Ruano, et al., *Proc. Natl. Acad. Sci. USA* 87, 6296–6300 (1990). This method is based on the idea of using a very low concentration of PCR primers for the first few cycles of PCR to increase specific product, and then boosting the concentration later.

The heat-releasable reagents of this invention are useful in this application. For example, a predetermined concentration of PCR primers "A and B" is entrapped in a heat-releasable reagent to melt at a predetermined temperature (i.e., 96°–100° C.). A reaction mixture is prepared with the target nucleic acid, any heat stable DNA polymerase, a suitably low concentration of the same PCR primers, A and B, and all other reagents needed for the reaction. Then, the sample is thermally cycled a few times under standard PCR conditions except the temperature is kept below the melting temperature of the entrapped primers (i.e., 90°–92° C.). After sufficient early cycles, the temperature is raised to melt the heat-releasable primer reagent and the PCR is continued as desired.

Alternatively, a "hot start" feature can be included by leaving the polymerase out of the initial reaction mixture. Instead, the polymerase to be used is entrapped in a second heat-releasable reagent that melts at a lower temperature (i.e., 70°–90° C.), than the entrapped primers. In this case, the PCR is only initiated when the entrapped polymerase is released and the same procedure is used.

Application G.
Nested PCR.

Nested PCR is another scheme for increasing the specificity of target DNA amplification, described by K. B. Mullis, et al., *Methods Enzymol.* 155, 335 (1987) and H. A. Erlich et al., *Science* 252, 1643–1651 (1991), among others. The strategy is to use one set of "outer" primers to initially amplify a segment of DNA that includes the target sequence, then add a second set of "inner" primers to specifically amplify the target sequence in the product the outer primers amplified. In the prior art, this has been done either by stopping the reaction to add the second set of primers, or by designing primers with certain sequences that effect their melting temperature (i.e., GC rich for high, AT rich for low). However, these problems can be avoided by using the heat-releasable reagents of this invention.

For example, a predetermined concentration of inner PCR primers "C and D" is entrapped in a heat-releasable reagent to melt at a predetermined temperature (i.e., 96°–100° C.). A reaction mixture is prepared with all the reagents needed for the reaction; the target nucleic acid, any heat stable DNA polymerase, and a suitably low concentration of outer PCR primers, A and B.

Then, the sample is thermally cycled a few times under standard PCR conditions, except the temperature is kept below the melting temperature of the entrapped inner primers (i.e., 90°–92° C.). After sufficient early cycles (preferably to consume most of the outer primers A and B), the temperature is raised to melt the heat-releasable reagent with the inner primers C and D. The PCR is continued as desired, to preferentially amplify the inner target sequence.

Alternatively, a "hot start" feature can be included by leaving the polymerase out of the initial reaction mixture. Instead, the polymerase to be used is entrapped in a second heat-releasable reagent that melts at a lower temperature (i.e., 70°–90° C.), than the entrapped primers. In this case, the PCR is only initiated when the entrapped polymerase is released and the same procedure is used.

Application H.

Other Types of PCR.

With suitable modification by one skilled in the art, the heat-releasable reagents of this invention can be applied to a wide variety of PCR methods. These include asymmetric PCR, inverse PCR and arbitrarily primed PCR (APPCR), among others. For example, this invention is readily adapted for use in in situ PCR, described by G. J. Nuovo, et al., *Amer. J. Pathol.* 139, 847–854 and 1239–1244 (1991).

The reagents of this invention are also applicable to inverted PCR (IPCR) as described by S. Takagi, et al., in *Biotechniques* 13, 176–178 (1992), and especially heat-soaked PCR (HS-PCR), as described by G. Ruano, et al., in *Biotechniques* 13, 266–274 (1992), but suitably modified so that a bolus of reagent would be added in a heat-releasable composition of this invention such as a waxy polymer bead.

Application I.

Nucleic Acid Hybridizations.

The heat-releasable reagents of this invention are useful in increasing specificity during certain nucleic acid hybridizations. For example, the labeled oligonucleotide probe is entrapped in any suitable heat-releasable reagent and added to the sample (i.e., nucleic acid immobilized to a membrane or to the inside surface of a container). The sample is heated to the desired temperature to melt the heat-releasable reagent and the probe becomes available for hybridization to the sample. After a suitable period, the unhybridized probe is washed away and the sample is handled by standard methods. The heat-releasable reagents of this invention can be utilized in a wide variety of hybridization procedures including in situ and "sandwich" hybridization, among others, and include any type of labeled probe, as described by M. S. Urdea, et al., *Nucleic Acids Res.* 16, 4937–4956 (1988), and others.

Application J.

Alkaline Phosphatase Label Detection Using Heat-Releasable Substrate Reagent.

In this example alkaline phosphatase (AP) is used for a label on any conventional specific binding substance such as a DNA, RNA or oligonucleotide probe, PCR primer, avidin or streptavidin, antibody, or antigen, among others. After the AP-labeled substance has been used in the appropriate binding reaction such as hybridization to complementary DNA or an antigen-antibody (i.e., ELISA) reaction, the bound substance is separated from the unbound. Separation can be done by binding to a solid support such as a membrane or the surface of a tube or well (i.e., sandwich immunoassay), or separation is done by various precipitation reactions, etc.

In any case, the presence of the AP label is detected by first immersing the enzyme in a suitable buffer such as AP buffer composed of 0.1M Tris HCl, 0.2M NaCl, 0.01M MgCl$_2$, pH 9.5–10. Then, a heat-releasable substrate reagent is added either with the AP buffer or afterwards. In this case, the heat-releasable reagent is concentrated substrate entrapped in any suitable waxy polymer or liposome that will melt at 40°–60° C. The substrate is a mixture of 5-bromo-4-chloro-3-indoyl phosphate (BCIP) and nitro blue tetrazolium (NBT).

When the sample is heated briefly to the melting temperature, the substrates are released to give approximately 0.17 mg/ml BCIP and 0.33 mg/ml NBT. The sample is incubated at a lower temperature to produce a colored product that is measured by absorption.

Application K.

Peroxidase Label Detection Using Heat-Releasable Substrate Reagent.

This example is similar to the hybridization and immunoassay methods for AP detection except that the label is any suitable peroxidase such as horseradish peroxidase, and the buffer is more acidic such as 0.1M sodium citrate, pH 5.0.

In this case, the heat-releasable reagent is concentrated o-phenylenediamine (OPD) entrapped in any suitable waxy polymer or liposome that will melt at 40°–60° C. When the sample is heated briefly to the melting temperature, the substrate is released to give approximately 0.1% OPD. The sample is incubated at a lower temperature to produce a colored product that is measured by absorption at 490 nM.

The following examples show the use of this invention in the PCR, which is one of several possible applications.

EXAMPLE I

Heat-Releasable Taq DNA polymerase Reagent Entrapped in Paraffin Wax

In this example, 0.01 ml of aqueous buffer containing 50 units of Taq DNA polymerase (Boehringer Mannheim Corp., Indianapolis, Ind.), was mixed with 0.1 gm of finely ground sucrose. The pH 8.0 buffer also contained 20 mM Tris-HCl, 1 mM dithiothreitol, 0.1 mM EDTA, 0.1 mM KCl, 0.5% Thesit, 0.2 mg/ml gelatine and 50% (v/v) glycerol. The solution may also include Mg$^{2-}$ as MgCl$_2$, and approximately 0.05–0.1% bromophenol blue. The mixture is partially dried to form small loose grains and mixed with approximately 0.5 gm of melted paraffin wax (64° C.). With the grains evenly distributed within, the melted wax mixture was cooled and solidified to form a flat disk approximately 2.5 cm diameter. Using a sharp blade, excess wax was trimmed from the edges and the disk was cut into approximately 2 mm diameter, dispensable particles that were washed by shaking in about 20 ml of water and soaked 20 minutes in a fresh volume of water. The particles were collected on absorbent paper, dried at room temperature and weighed.

The amount of particles to use in a particular reaction is calculated from the amount of polymerase in the total weight. In this example, there were 5 units of enzyme in a total weight of 0.32 gm. To use 1 unit of the entrapped enzyme, a 1/50 fraction is needed, or approximately 0.0064 gm of particles.

The entrapped DNA polymerase reagent was tested in the PCR using commercially available "PCR buffer" (Boehringer Mannheim). The DNA (template) to be amplified was Lambda bacteriophage DNA from Sigma Chemical Corp. St. Louis, Mo. The 25 base oligonucleotide primers were "Lambda control primers" #1 and #2 (Perkin-Elmer Cetus, Norwalk, Conn.), which complement the ends of a 500 base pair segment on the Lambda DNA, nucleotides 7131 through 7630.

A PCR "master mix" was prepared in PCR buffer without DNA polymerase, to give 4 mM MgCl$_2$, 0.4 mM each of dATP, dCTP, dGTP, and dTTP (dNTP's), 0.002 micrograms of Lambda DNA, 2 microliters (0.04 nanomoles) of each primer #1 and #2 for each reaction volume of 0.05 ml. After dispensing 0.05 ml of master mix into each of three sample containers, DNA polymerase was added as follows:

Sample A received 0.012 gm (2 units), and sample B received 0.024 gm (4 units), of paraffin entrapped Taq DNA polymerase reagent. Sample C received 1 unit of standard un-entrapped Taq DNA polymerase as a control.

The samples were thermocycled for 30 cycles of; 30 seconds @ 94° C., 30 seconds @ 40° C., and 60 seconds @ 72° C.

The PCR products were analyzed by a standard method of agarose gel electrophoresis (AGE). The samples A, B and C were loaded into corresponding wells A, B and C. The AGE was done horizontally using 2% agarose gel and 89 mM tris, 89 mM borate, 2 mM EDTA (TBE) buffer (pH 8), containing 0.5 micrograms/ml of ethidium bromide stain. The gel was run for 1 hour at 100 volts and 50 milliamps, then subilluminated with U.V. light and photographed with Polaroid instant film.

AGE analysis of PCR samples with master mix alone gives no visible product (data not shown). However, as is shown in FIG. 1, lanes A, B and C, visible product bands can be seen at the top of each lane. These results indicate that the paraffin entrapped Taq DNA polymerase reagent in samples A and B was released from entrapment during the PCR and successfully amplified the Lambda DNA compared to control C.

AGE Method For Samples In A 96 Well Format.

Higher numbers of samples can be analyzed when loaded directly from the PCR tubes into the agarose gel for electrophoresis. It has been discovered that this is greatly facilitated by using specially designed combs for making the sample wells in the gel. As described in Disclosure Document #291836, the key feature is that the combs were made with teeth that are spaced with 4.5 mm centers. This spacing is one half the normal 96 well or microtiter format (9 mm centers), found in PCR thermocyclers such as the Perkin Elmer Model 9600 and the microplate cyclers sold by Techne Corp. and MJ Research, Mass. Typically, combs are used that are 1–3 mm thick with teeth cut 2.5 mm wide, leaving 2 mm spaces between. However, other teeth dimensions that fit within the 4.5 mm center to center requirement would be suitable. Also, the combs can be made of any suitable plastic commonly used for AGE, as well as other materials used for special applications.

The resulting wells formed at 4.5 mm centers provide twice as many wells as there are microwell samples, in the same distance. Solutions are conveniently transferred from the microwells and loaded into the gel wells with the use of a standard multichannel pipet (i.e., Labsystems, Mass., or Brinkmann Instruments, Inc., N.Y.). However, this method works best when a pair of rows of microwell (9 mm spacing), samples are both loaded into the same gel row using alternate wells.

For instance, microwell samples of:

| A1 | A2 | A3 | A4 | A5 | A6 | A7 | A8 | etc. |
| B1 | B2 | B3 | B4 | B5 | B6 | B7 | B8 | etc. | transferred to alternate wells in one row of the gel give:

| A1 B1 A2 B2 A3 B3 A4 B4 A5 B5 A6 B6 A7 B7 A8 B8 etc. |

The result is that twice as many sample can be run in the gel, which saves space and use of the gel.

Also, the 4.5 mm spacing format can easily be adapted for use in other electrophoresis methods. For instance, in vertical acrylamide gels that employ "shark's tooth" combs, the teeth would be made at 4.5 mm centers. This format can also be applied to capillary electrophoresis by arranging the electrophoresis sampling cups with 4.5 mm spacing and/or the capillary tubes themselves at 4.5 mm spacing.

EXAMPLE II

Heat-Releasable dNTP Reagent Using a Paraffin Wax Coating

In this example, 0.02 ml of water containing 25 mM each of dATP, dCTP, dGTP and dTTP, is mixed with 0.1 gm of finely ground sucrose. The solution may also include an equimolar amount of $Mg^{2-}$ as $MgCl_2$, and approximately 0.05–0.1% bromophenol blue. The mixture is dried to form small loose grains and mixed with approximately 0.5 gm of melted paraffin wax (64° C.). With the grains evenly distributed within, the melted wax mixture was cooled and solidified to form a flat disk approximately 2.5 cm diameter. Using a sharp blade, the disk was cut into approximately 2 mm diameter particles that were washed by shaking in about 20 ml of water and soaked 20 minutes in a fresh volume of water. The particles were collected on absorbent paper, dried at room temperature and weighed.

The amount of particles to use in a particular reaction is calculated from the amount of dNTP's in the total weight. In this example, there was 0.5 micromoles of each dNTP in a total weight of 0.546 gm. To use 0.02 micromoles of the entrapped dNTP, a 1/25 fraction is needed, or approximately 0.022 gm of particles.

The entrapped dNTP reagent was tested in the PCR using commercially available "PCR buffer" (Boehringer Mannheim Corp., Ind.). The DNA (template) to be amplified was Lambda bacteriophage DNA from Sigma Chemical Corp. The 25 base oligonucleotide primers were "Lambda control primers" #1 and #2 (Perkin-Elmer Cetus, Conn.), which complement the ends of a 500 base pair segment on the Lambda DNA, nucleotides 7131 through 7630.

A PCR "master mix" was prepared in PCR buffer without any dNTP's, to give 1 unit Taq DNA polymerase, 4 mm $MgCl_2$, 0.002 micrograms of Lambda DNA, 2 microliters (0.04 nanomoles) of each primer #1 and #2 for each reaction volume of 0.05 ml. After dispensing 0.05 ml of master mix into each of two sample containers, dNTP's were added as follows:

Sample D received 0.01 gm, and sample E received 0.02 gm of paraffin entrapped dNTP reagent.

The samples were thermocycled for 30 cycles of; 30 seconds @ 94° C., 30 seconds @ 40° C., and 60 seconds @ 72° C.

The PCR products were analyzed by a standard method of agarose gel electrophoresis (AGE). The samples D and E were loaded into corresponding wells D and E.

The AGE was done horizontally using 2% agarose gel and TBE buffer containing 0.5 micrograms/ml of ethidium bromide stain as in Example I. The gel was run for 1 hour at 100 volts and 50 milliamps, then subilluminated with U.V. light and photographed with Polaroid instant film.

As is shown in FIG. 1, visible product bands can be seen at the top of lanes D and E. These results indicate that the paraffin entrapped dNTP reagent in samples D and E was released from entrapment during the PCR and was successfully used as a substrate to amplify the Lambda DNA.

EXAMPLE III

Heat-Releasable dNTP Reagent Using Beeswax Coated Pellets

In this example, 0.02 ml of water containing 25 mM each of dATP, dCTP, dGTP and dTTP, is mixed with 0.1 gm of finely ground sucrose. The solution may also include an equimolar amount of $Mg^{2-}$ as $MgCl_2$, and approximately 0.05–0.1% bromophenol blue. The mixture is dried to form small loose grains and mixed with approximately 0.5 gm of melted beeswax (80° C.). With the grains pushed out of the center to form a circle, the melted wax mixture was cooled and solidified to form a flat disk approximately 2.5 cm diameter. Using a sharp blade, the disk was trimmed of wax without entrapped grains and cut into pellets of approximately 1×2×4 mm that were washed by shaking in about 20 ml of water and soaked 20 minutes in a fresh volume of water. The pellets were collected on absorbent paper, dried at room temperature and weighed.

The number of pellets to use in a particular reaction is calculated from the amount of dNTP's in the total number of equal sized pellets. In this example, there was 0.5 micromoles of each dNTP in a total weight of 0.418 gm. The average pellet weight was 0.011 gm., which is approximately 0.013 micromoles of the entrapped dNTP per pellet.

The entrapped dNTP reagent was tested in the PCR using commercially available "PCR buffer" (Boehringer Mannheim Corp., Ind.). The DNA (template) to be amplified was Lambda bacteriophage DNA from Sigma Chemical Corp. The 25 base oligonucleotide primers were "Lambda control primers" #1 and #2 (Perkin-Elmer Cetus, Conn.), which complement the ends of a 500 base pair segment on the Lambda DNA, nucleotides 7131 through 7630.

A PCR "master mix" was prepared in PCR buffer without any dNTP's, to give 1 unit Taq DNA polymerase, 4 mm $MgCl_2$, 0.002 micrograms of Lambda DNA, 2 microliters (0.04 nanomoles) of each primer #1 and #2 for each reaction volume of 0.05 ml. After dispensing 0.05 ml of master mix into the sample container, sample F received 1 pellet of beeswax entrapped dNTP reagent.

The sample was thermocycled for 30 cycles of; 30 seconds @ 94° C., 30 seconds @ 40° C., and 60 seconds @ 72° C.

The PCR product was analyzed by a standard method of agarose gel electrophoresis (AGE). Sample F was loaded into corresponding well F.

The AGE was done horizontally using 2% agarose gel and TBE buffer containing 0.5 micrograms/ml of ethidium bromide stain as in Example I. The gel was run for 1 hour at 100 volts and 50 milliamps, then subilluminated with U.V. light and photographed with Polaroid instant film.

As is shown in FIG. 1, a faint but visible product band can be seen at the top of lane F. These results indicate that the beeswax entrapped dNTP reagent in samples F was released from entrapment during the PCR and was successfully used as a substrate to amplify the Lambda DNA.

EXAMPLE IV

PCR With Liposomes and Taq DNA Polymerase

Liposomes with entrapped Taq DNA polymerase were prepared by first evaporating a lipid mixture containing 0.2 ml of 0.078 gm/ml soybean lecithin and 0.05 ml of 0.074 gm/ml cholesterol, on one half of the inside wall of a glass vial (22 mm diameter×45 mm high), held on its side. To the dried lipid layer was added 0.08 ml of 0.02% bromophenol blue in Hank's balanced salt solution (HBSS) and 0.02 ml of Taq buffer containing 100 units of Taq DNA polymerase (Boehringer Mannheim Corp., Ind.). The Taq buffer also contained 20 mM Tris-HCl, 1 mM dithiothreitol, 0.1 mM EDTA, 0.1 mM KCl, 0.5% Thesit, 0.2 mg/ml gelatine and 50% (v/v) glycerol. Liposomes were allowed to form as the vial was gently rolled on its side for 5–10 minutes. The turbid solution was forced back and forth through an Eppendorf pipette tip 8–10 times and centrifuged to pellet the liposomes. The liposomes were washed twice by resuspending in 1.5 ml HBSS and centrifuging as before, finally resuspending them in 0.012 ml HBSS.

The liposome entrapped DNA polymerase reagent was tested in the PCR using commercially available "PCR buffer" (Boehringer Mannheim). The DNA (template) to be amplified was Lambda bacteriophage DNA from Sigma Chemical Corp., Mo. The 25 base oligonucleotide primers were "Lambda control primers" #1 and #2 (Perkin-Elmer Cetus, Conn.), which complement the ends of a 500 base pair segment on the Lambda DNA, nucleotides 7131 through 7630.

A PCR "master mix" was prepared in PCR buffer without DNA polymerase, to give 4 mm $MgCl_2$, 0.4 mM each of dATP, dCTP, dGTP, and dTTP (dNTP's), 0.002 micrograms of Lambda DNA, 2 microliters (0.04 nanomoles) of each primer #1 and #2 for each reaction volume of 0.05 ml. After dispensing 0.05 ml of master mix into each of two sample containers, liposome entrapped DNA polymerase was added as follows:

Sample G received 3 microliters and sample H received 9 microliters, of the liposome entrapped Taq DNA polymerase suspension.

The samples were thermocycled for 30 cycles of: 30 seconds @ 94° C., 30 seconds @ 40° C., and 60 seconds @ 72° C.

The PCR products were analyzed by a standard method of agarose gel electrophoresis (AGE). The samples G and H were loaded into corresponding wells G and H.

The AGE was done horizontally using 2% agarose gel and TBE buffer containing 0.5 micrograms/ml of ethidium bromide stain as in Example I. The gel was run for 1 hour at 100 volts and 50 milliamps, then subilluminated with U.V. light and photographed with Polaroid instant film.

No visible product was detected (data not shown). To each sample G and H, was added 4 units of un-entrapped Taq DNA polymerase, the PCR cycles were repeated and the samples again analyzed by AGE as before.

As is shown in FIG. 1, visible product bands can be seen at the top of lanes G and H. These results indicate that soybean lecithin and cholesterol liposomes are usable in the PCR.

EXAMPLE V

Waxy Polymer Coated Drop Beads Made by Dropping Them Through Melted Wax

In this example, waxy coated liquid droplets, called "drop beads", were made by dropping liquid through melted wax. Approximately 3 microliter sized droplets of heat-releasable reagent were dropped through a thin molten waxy polymer layer on the surface of a water bath and were instantly coated after passing through the wax layer and sinking to the bottom. The resulting wax coated beads were spherical and had very thin wax shells, with diameters of approximately 3–4 mm.

A tall glass beaker (top diameter 6.7 cm, height 14 cm), was filled to the top with distilled water, and placed in a 1 L beaker partially filled with water. After the two water levels were evened, a submersible heater was used in the outer bath to heat the top 6–7 cm of the outer and inner baths to boiling (94°–95° C.). A temperature gradient was achieved by submersing the lower 5–6 cm of the entire beaker assembly in an ice bath. A 7–10 cm deep heat zone was formed that ranged from 95° C. at the top to 75° C. at the bottom. Below the heat zone, (approx. 4 cm remaining) it was 40°–15° C. After the system was equilibrated, one gram of paraffin wax (m.p. 68°–74° C., Fluka Chemical Corp.), was added to the inner bath and gently stirred until the wax melted and formed a uniformly thick "puddle" over the entire surface.

The dropping solution consisted of heat-releasable reagent (horseradish peroxidase enzyme, 1 unit/microliter of phosphate buffer) in a 2:1 sucrose solution (2 g sucrose/1 g distilled water) with a suitable amount (1 drop/10 ml) of commercial food coloring. The color was useful in showing that the dropping solution was being entrapped in the drop beads and also helped in showing possible imperfections in the wax coating.

Small droplets were formed using a 30–35 gauge plastic tubing (i.e., gel loading pipet tips work well) attached to a 1 ml syringe. With the syringe held vertically, droplets were released 8–9 cm above the center zone (3–4 cm diameter) of the wax layer, every 5–6 seconds. After 50 beads were made the wax layer was replenished by adding 0.14 g of new wax (approx. 0.0028 gm wax consumed/bead). The dropping solution was maintained at room temperature.

An oil layer covering the outer bath surface helped reduce evaporation and the two levels were held constant for several hours. This helped keep temperatures in the inner bath constant. A lower water level in the outside beaker changes the heating zone for the inside bath and this should be avoided. For example, a cooler temperature around the wax puddle usually resulted in droplets sticking if the droplet densities or dropping heights were not increased.

After about 150 drop beads were made the system was allowed to cool and the beads were removed by pouring them out into a paper or polypropylene filter. The beads were then washed several times with distilled water and then brushed out onto a paper towel to dry.

The beads were tested for total volume by puncturing the bead and drawing the contents into a precalibrated 10 microliter capillary pipet (Drummond). Beads typically contained an average volume of 2.6 microliters.

The average amount of wax in each bead was calculated from the weight of washed and dried wax from 5–10 beads. The average amount of wax per bead was typically 2.8 mg.

Many parameters such as dropping height, dropping solution density vs. droplet size, temperature, and wax puddle thickness effect drop bead formation. These parameters all effect how well the droplets punch through the puddle and the quality of the coatings that result. Dropping heights that are too high generally cause bubbles at the tops of the beads which expand as the newly formed beads sink and the beads ultimately rise again to remelt. High dropping solution densities are generally better (i.e., using sucrose:water at greater than 2:1 ratio), because the droplets easily punch through the puddle. Puddle thickness and dropping height also effect the ability of the droplet to punch through and temperature effects the strength of the wax (high temperature makes the wax more fluid). Puddles that are too thin generally result in incomplete coating. To make drop beads consistently, all of these parameters are optimized because they are interdependent.

Waxy polymer drop beads have been made using many different sized containers and heating devices. Deeper baths were used to vary the heat zone depth and in some cases deeper heat zones were necessary to completely seal the wax coating on larger beads (10–50 microliters). Larger diameter wax puddles increased the number of beads that could be made in a batch without replenishing wax.

Double Coated Drop Beads

Thicker coatings can readily be applied to the drop beads with "double dipping". This was done by dropping waxy polymer beads through another molten paraffin wax layer. The second wax layer was a lower melting point wax (i.e., 5°–10° C. lower). This allowed for the temperature of the bath to be lowered and the first layer of wax on the bead would remain solid. Multiple layers of wax can be applied by dropping or dipping beads into molten wax at slightly lower temperatures than the melting point of the previous wax used.

Testing Drop Beads

Drop beads were tested for encapsulation of horseradish peroxidase (HRP) enzyme. In this example the permeability of double coated beads was compared with single coated beads. The general procedure was to make drop beads using the method described previously where the dropping solution contained 1 unit per microliter concentration of enzyme in a 2:1 sugar solution. After the beads were rinsed and dried, 36 of the single coated beads and 36 of the double coated beads were selected and transferred to a 96 well plate. Two drops (approx. 100 microliters) of 0.1M phosphate buffered saline, pH 6 (PBS) was added to each well and the beads were soaked in the buffer for 40 minutes to permit possible leakage.

A standard curve of diluted HRP was simultaneously set up in separate wells to estimate relative concentrations of enzyme that may have leaked into each of the test wells. A two fold serial dilution of enzyme was prepared in 100 microliters/well of PBS, to give approximately 10, 5, 2.5, 1.25, 0.625, 0.31, 0.16, 0.08, 0.04, 0.02, 0.01 and 0.005 units/well, that were numbered 1 through 12, respectively.

Then, two drops of the HRP substrate O-phenyldiamine (OPD, 2 mg/ml) and one drop of hydrogen peroxide (0.03%) was added to all wells. Color developed in some wells after approximately 10 minutes, indicating the amount of enzyme present. In the standard curve, wells from 1 to 8 were dark orange. The remaining wells ranged from orange (#9) to very faint yellow (#12), which was considered the borderline between leakage and no detectable leakage. Four control wells without enzyme or beads added, had no color.

The color of each solution in test wells containing beads was then compared to the standard curve wells and assigned a score. A score of less than 12 indicated that detectable enzyme had leaked from the bead.

| HRP Drop Bead Test Results | | | | | | |
|---|---|---|---|---|---|---|
| Standard Well# | <9 | 9 | 10 | 11 | 12 | |
| Units Per Well | >0.08 | 0.04 | 0.02 | 0.01 | 0.005 | 0 |
| Color | dark orange | orange | yellow | light yellow | faint yellow | no color |
| One Coat Beads | 27 | 3 | 3 | 3 | 0 | 0 |
| Two Coat Beads | 0 | 0 | 0 | 0 | 2 | 34 |

These results show that waxy polymer coated drop beads can be made that encapsulate enzyme with very little leakage. Also the data show that the double coated beads encapsulated more effectively than the single coated beads, with most of them showing no detectable leakage.

EXAMPLE VI

Injected Beads Made By Injecting Heat-Releasable Reagent Into Melted Waxy Polymer In this example, waxy coated liquid droplets, called "injected beads", were made by injecting heat-releasable reagent into molten beads of waxy polymer. One microliter volumes of heat-releasable reagent were entrapped in molten wax and cooled to form beads that were semi-spherical and had diameters of 3–4 mm. The volume of solution entrapped was restricted by the volume of the molten wax, and by the precision of the injection.

The injection apparatus consisted of two syringes, one for dispensing molten wax beads and the other for injecting the molten wax with heat-releasable reagent. The wax dispensing syringe (5 ml volume) was mounted on a heating rod (18 watt curling iron), and fitted with an 18 gauge stainless steel needle, also in contact with the heating rod. It was filled with molten paraffin wax (m.p. 68°–74° C., Fluka Chemical Corp.).

The reagent injecting syringe was a "gastight" 50 microliter syringe mounted on a push button, PB600 repeating dispenser (both from Hamilton Co., Reno, Nev.), and fitted with a few centimeters of 30 gauge teflon tubing. The reagent injecting syringe assembly was separate from the heated wax dispensing syringe, but the end of the teflon tubing was held in a small copper wire loop that was mounted on the heating rod. This permitted the wire loop and the teflon tubing tip to be heated near, or above, the wax melting temperature. The wax dispensing needle and the teflon tubing were positioned about 0.5–2 cm apart and parallel, with the injection tubing positioned so that injection would be vertical.

The forming surface was a thin plastic film, adhered to the surface of a metal (aluminum, stainless steel) plate. Strips of polyethylene (Saran wrap) were carefully pressed on top of a water droplet to form a seal against the metal. This surface was flat and easily replaced with a clean film after each use.

A variety of heat-releasable reagent compositions were used for injection. For HRP injected beads, HRP enzyme in water or suitable phosphate buffer, and 0.05–0.2% food coloring worked well. For Taq injected beads, Taq DNA polymerase enzyme (5 units/microliter), in the vendor's storage buffer (Boehringer Mannheim Corp., Indianapolis, Ind.), was used. Generally, the vendor's Taq solution was diluted by 1/3.3 into a "Taq diluent" consisting of; 1 ml of 75% glycerol in H$_2$O (pH 7.5), 0.15 ml of 0.2M Tris-EDTA (pH 8), 0.15 ml of 1M KCl and 0.2 ml of 0.4–0.5 mg/ml cresol red. This gave a final concentration of 1.5 units/ml Taq.

To make the injected beads, the steps were:

(1) dispense molten wax (10–50 microliters) to form a liquid wax bead on the plastic film, which cools the bottom of the bead causing it to slowly solidify from the bottom up;

(2) while the bead is still molten, push the heated tip of the injector tubing vertically into the top center of the molten bead;

(3) inject the wax with heat-releasable reagent (1–5 microliters) and remove the tubing.

The injected beads are then allowed to cool to form a completely solid, waxy polymer coating around the injected reagent.

FIG. 2 is a cross-sectional diagram showing a molten bead formed on a flat surface 18, after injection of heat-releasable reagent 12, and before the injector tube 10 has been removed. The outer waxy polymer 16, then cools and solidifies.

FIG. 3 is a cross-sectional diagram showing a molten bead formed on a flat surface 18, by dispensing molten waxy polymer 16 from a heated dispenser tube 14. The diagram also shows an injector tube 10 leading through, and concentric with, the heated dispenser tube. This is one useful arrangement for keeping the injector tip warm enough to prevent sticking to the waxy polymer. Injection of heat-releasable reagent 12, has just been completed, before the tubing assembly is removed. The outer waxy polymer 16, then cools and solidifies.

An important parameter in making injected beads is centering the injected droplet in the molten wax bead. Centering results in maximum wax thickness between the entrapped droplet and the outside. This is accomplished by inserting the injector tip vertically into the top center of the bead and waiting (0.1–1 second) for the bottom of the wax bead to cool and slightly solidify before injection which prevents the injected reagent from sinking through the bottom. The metal plate under the plastic surface was useful in reducing static electricity problems and for cooling the bottom of the beads.

Testing Injected Beads

Injected beads were tested for encapsulation of HRP using a similar method to that used for the HRP drop beads. Injected beads were made injecting 1 microliter of solution (approx. 0.137 units HRP per microliter in 50% glycerol and 0.1% food coloring, Schilling) by the same procedure as described above. The beads were washed and 54 were placed in a 96 well plate and soaked in 3 drops of PBS for approximately 1 hour. A standard curve of two-fold diluted HRP was prepared in separate wells to contain; 0.0685, 0.034, 0.017, 0.0086, 0.0043, 0.0021, 0.0011 and 0.00054 units/well, and numbered 1 through 8.

After soaking, 2 drops of OPD substrate (2 mg/ml) were added followed by 1 drop hydrogen peroxide (0.03%). The standard curve wells developed a color gradient down to approximately 0.0043 units per well, but no color was evident in any of the test wells with injected beads. Control wells prepared without enzyme or beads added, also had no color.

| HRP Injected Bead Test Results | | | | | | | |
|---|---|---|---|---|---|---|---|
| Standard Well# | <3 | 3 | 4 | 5 | 6 | 7 | 8 |
| Units Per | >0.017 | 0.017 | 0.0086 | 0.0043 | 0.0021 | 0.0011 | 0.00054 |
| Well Color | dark yellow | yellow | light yellow | faint yellow | no color | no color | no color |
| Bead Distribution | 0 | 0 | 0 | 0 | 54 | | |

These results show that waxy polymer coated injected beads can be made that encapsulate enzyme with no detectable leakage.

Some of the HRP injected beads were subsequently used to show that heating the beads to melting temperature (above 72° C.), releases active enzyme.

Six of the injected beads were placed in small glass tubes containing a few drops of distilled water and heated over a hot plate until melted. Then a few drops of OPD substrate and hydrogen peroxide were added. Fifty percent of the vials showed orange color indicating enzyme activity.

These results indicate that the HRP injected beads can be used to entrap enzyme and that the enzyme remains active as a heat-releasable reagent.

A PCR test was run to determine the viability of DNA polymerase (Taq) enzyme in injected beads. Taq injected beads were prepared as previously described.

The PCR procedure was similar to that described previously. The temperature cycling was done in 3 separate water baths at 95° C., 72° C., and 54° C. Capped centrifuge tubes (0.25 ml) were used as reaction vessels and were placed in a plastic pipette rack so that they could be transferred to and from each bath conveniently. Each tube received a total volume of 25 microliters consisting of 10.5 microliters sterile water, 12.5 microliters of 2× buffer to give final approximate concentrations of 2.5 mM $MgCl_2$, 0.15 mM dNTP's, 2% Ficoll, 0.002% xylene cyanole FF and 0.05% BSA. Also added was 2 microliters each of pBR322 DNA template (2 ng), and $10^{-6}$M pBR322 primers BamH I, and Pst I (all from Sigma Chem. Co.).

After these solutions were dispensed, each control sample had Taq enzyme added in solution and a drop of mineral oil was added to reduce evaporation. Each test sample had Taq added only as heat-releasable reagent within a Taq injected bead. Each Taq injected bead contained 1 microliter of solution (1.5 units of Taq in storage buffer with glycerol and cresol red, described previously).

The samples were cycled 35 times, with 2 minutes each of; denaturation at 95° C., annealing at 54° C., and extension at 72° C. After cycling, 5 microliters of all 9 control samples but only 5 of the bead each sample was transferred to a 2% agarose gel and electrophoresed in Tris borate EDTA buffer (TBE, pH 8.5), containing ethidium bromide, at approximately 50 volts, 500 milliamps for 45 minutes. The gel showing bands of separated products was observed by subillumination using a U.V. lamp, and photographed through an orange filter.

The results from a selected group of samples were that eight (89%) out of nine controls tested showed amplified product. All five (100%) of the five Taq injected bead samples tested showed amplified product. The results of experiments with HRP or Taq injected beads show that different enzymes are readily encapsulated within, and heat-released from the injected beads of this invention.

EXAMPLE VII

Injected Beads Made By Injecting Into Melted Waxy Polymer Held In A Mold

In this example, the previous method for making injected beads was improved by making injected beads in small plastic cups or molds. The molds were rounded depressions (1.5–3 mm diameter and 1–2 mm deep) in thin plastic sheets made by overlaying a perforated plastic or metal plate with a thin plastic sheet (polyethylene or polypropylene) and using heat and vacuum to pull the plastic into the perforations, then cooled.

For the new method using a mold, the steps were:

(1) dispense molten wax (10–50 microliters) to form a liquid wax bead that rests on the bottom of the mold, and touches at least part of the sides of the mold surface;

(2) while the bead is still molten, push the heated tip of the injector tubing vertically into the top center of the molten bead:

(3) inject the wax with heat-releasable reagent (1–5 microliters) and remove the tubing.

The injected heads are allowed to cool to form a solid, waxy polymer coating around the injected reagent.

FIG. 4 is a cross-sectional diagram showing a molten bead formed in a cup or mold 20, by dispensing molten waxy polymer 16 from a heated dispenser tube 14. The diagram also shows an injector tube 10 in parallel and in contact with, the heated dispenser tube. This is a useful arrangement for keeping the injector tip warm enough to prevent sticking to the waxy polymer. Injection of heat-releasable reagent 12, has just been completed, before the tubing assembly is removed. The outer waxy polymer 16, then cools and solidifies to form a rounded bottom.

Results

Injected beads formed in a mold had more consistent centering of injected reagent, which reduced potential leakage through the wax. The mold worked better apparently because the curvature of the mold tended to cool and slightly solidify the sides of the molten bead as well as the bottom, keeping the injected reagent in the center. It was also found that suitable injected beads can be made in a strip of molds similar to that shown in FIG. 6. In this example the molds used were strips of hollow, plug-strip caps (Life Science Products Inc., cat# LS 5610). The hollow part of the cap was used as the mold. These polyethylene caps are normally used on micro-titer tubes and are spaced at 9 mm centers.

It was also found that a suitable sleeve to cover the strip caps can be made by laying a strip of clear plastic (acetate) over a strip of strong paper and heat sealing along the edges to form flat tubing with one side plastic and the other paper. Suitable material for this was cut from a "Durapeel" autoclavable pouch (Baxter Healthcare Corp., Calif.). The flat tubing was then slipped over the cap (mold) strips containing the beads and heat sealed at the ends. A variety of other tubing (i.e., extruded), of the proper size would be suitable.

To dispense the beads into a row of tubes or wells (i.e., 96 well format), one end of the sleeve is cut off. Then, the entire strip of molds, with beads, is inverted over the tubes and the sleeve is pulled away to let the beads drop into the tubes. It was also found that the strip mold and sleeve assembly can be used simply as a container for other beads such as drop beads.

Multiple Dispensing And Injection

The injection methods disclosed for making the waxy polymer coated heat-releasable reagents of the instant invention are readily adapted to complete or semi-automated procedures. FIG. 5 is a diagram of a device for multiple dispensing of molten waxy polymer beads and injecting them with heat-releasable reagent. The molten waxy polymer is contained in syringes 22, that are kept heated at or above the waxy polymer's melting temperature by heating element 24, which also would be configured to keep the dispenser tubes heated. When the dispenser plungers 26, are pushed down, melted waxy polymer beads are extruded from the dispenser tubes 14. Then, heat-releasable reagent is injected through injector tubes 10, from injector syringes 28, by pushing on injector plungers 30. Suitably, the plungers 26 and 30 are connected to and controlled by precise driving mechanisms such as precision screws that are turned by electronically controlled step motors to dispense microliter volumes consistently. Any suitable number of syringes can be included in this system, preferably with the dispenser and injector tips spaced to fit commercially used formats. Most preferred are sets of 4, 6, 8 or 12 tip assemblies spaced at 9 mm centers to correspond with standard microwell or microtiter formats. Also preferred would be spacing at 4.5 mm to correspond with the new electrophoresis gel combs disclosed herein. In any case, the multiple dispensing and injecting can be done on a variety of stationary or movable surfaces, and include the use of cups or molds as previously described.

EXAMPLE VIII

Dipped-Liquid Beads

Suitable beads can also be made by dipping liquid droplets into molten waxy polymer to coat them. In this example, an aqueous solution of 2:1 sucrose to water, containing approximately 0.1% food coloring was used. A hanging droplet of 2–4 microliters was formed on the end of small (2–3 mm O.D.) plastic tubing (i.e., on a syringe), and cooled in a freezer until suitably viscous (or sometimes frozen in a dry ice chamber). Then, the droplet and tubing was dipped into molten paraffin wax approximately 1–3 mm above the droplet, and quickly removed to let solidify. This was repeated 2–4 times to form an encapsulated droplet. When the entrapped droplet is pulled off of the tubing, it has a narrow wax "neck" from where the tubing was. With the droplet held upright, the neck is gently heated with a hot wire to re-melt only the wax neck and thereby seal the top. These colored liquid filled beads were tested for leakage by soaking them in water several days and no loss of coloring was seen. This method could be automated and used for entrapment of the heat-releasable reagents of this invention.

EXAMPLE IX

Wax Tubes Containing Heat-Releasable Reagent

This example shows that any suitable aqueous liquid can be entrapped in fine wax tubes and the tubes can be cut to a certain length and simultaneously sealed to make small dispensable packages. In this example, a small wax tube was made by dipping a cold needle into molten wax in a hot water bath. Several coatings could be achieved by cooling the wax tube before each dip. After 2–3 coatings and while the wax was still warm, the wax tube was removed by pushing it off the needle while still warm. The tube was then injected with colored water and the ends were sealed by heating with a hot wire. No leakage occurred after immersion of the container in cold water.

From the foregoing, it will be appreciated that adding a preformed wax bead that contains a heat releasable reagent, according to the present invention, avoids prior art layering problems by eliminating the need for the reaction tube as a container for making a barrier between subsets of PCR reagents. It was surprising to discover that wax-insoluble enzymes and other reagents could be suspended in wax beads, before any exposure to aqueous solutions, thereby permitting their use in PCR, RTR, DNA sequencing procedures, and other high temperature in vitro procedures. Furthermore, it was found that reagents having very low solubility are preferred because they are readily released from the wax upon heating. The use of waxes with high melting points permits one to optimize the reaction temperature of the desired in vitro procedure.

While the invention has been described with references to certain specific embodiments, it is understood that changes may be made by one skilled in the art and it would not thereby depart from the spirit and scope of the invention which is limited only by the claims appended hereto.

What is claimed is:

1. An in vitro reaction method comprising the steps of:
    (a) adding a dispensable body containing a reagent to an aqueous medium containing a substance capable of reacting with said reagent, said dispensable body containing the reagent being prepared by entrapping an aqueous suspension of a reagent in a water insoluble and water impermeable wax bead having a melting temperature greater than 40° C., wherein the aqueous suspension of the reagent is entrapped in the water insoluble and water impermeable wax bead by dropping droplets of the aqueous suspension through a molten layer of the wax whereby the droplets are coated with the wax as the droplets pass through the layer of molten wax and passing the wax-coated droplets to a cooling zone where the wax is solidified to form beads of wax with the reagent entrapped within the beads; and
    (b) heating the dispensable body containing the reagent to a temperature at which the wax bead melts and releases the entrapped reagent into the aqueous medium, wherein the reagent reacts with the substance in the aqueous medium.

2. The method of claim 1, wherein the entrapped reagent is a heat resistant enzyme.

3. The method of claim 1, wherein the entrapped reagent is an enzyme substrate.

4. The method of claim 1, wherein the entrapped reagent is a metal salt.

5. The method of claim 1, wherein the entrapped reagent is a labeling substance.

6. The method of claim 1, wherein the in vitro reaction is a polymerase chain reaction (PCR), wherein the entrapped reagent is a heat resistant DNA polymerase, and wherein the substance capable of reacting with the entrapped reagent in the aqueous medium is a nucleic acid.

7. The method of claim 1, wherein the in vitro reaction is a polymerase chain reaction (PCR), wherein the entrapped reagent is an enzyme substrate selected from the group consisting of nucleoside triphosphates (NTP's), deoxynucleoside triphosphates (dNTP's), and dideoxynucleoside triphosphates (ddNTP's), wherein the substance capable of reacting with the entrapped reagent in the aqueous medium is a polymerase enzyme, and wherein the melting temperature of the wax bead is in the range from 50° C. to 100° C.

8. The method of claim 1, wherein the in vitro reaction is a high temperature reverse transcriptase reaction (RTR), wherein the entrapped reagent is selected from reverse transcriptases, Tth DNA polymerase, and deoxynucleoside triphosphates (dNTP's), wherein the substance capable of reacting with the entrapped reagent in the aqueous medium is a nucleic acid, and wherein the melting temperature of the wax bead is about 70° C.

9. The method of claim 1, wherein the in vitro reaction is high temperature nucleic acid sequencing, wherein the entrapped reagent is selected from heat resistant enzymes and a labeling mixture of deoxynucleoside triphosphates (dNTP's), wherein the substance capable of reacting with the entrapped reagent in the aqueous medium is a nucleic acid, and wherein the melting temperature of the wax bead is higher than the temperature at which the template becomes fully denatured.

10. The method of claim 1, wherein the in vitro reaction is coupled high temperature reverse transcriptase reaction (RTR) and polymerase chain reaction (PCR), wherein the entrapped reagent includes a chelating agent, MgCl$_2$, and forward and reverse PCR primers, wherein the substance capable of reacting with the entrapped reagent in the aqueous medium is a nucleic acid, and wherein the melting temperature of the wax bead is in the range from about 50° to about 100° C.

11. The method of claim 1, wherein the in vitro reaction is nucleic acid hybridization, wherein the entrapped reagent is an oligonucleotide, and wherein the substance capable of reacting with the entrapped reagent in the aqueous medium is a nucleic acid.

12. The method of claim 1, wherein the in vitro reaction is alkaline phosphatase label detection, wherein the entrapped reagent is a phosphorylated substrate, and wherein the substance capable of reacting with the entrapped reagent in the aqueous medium is an alkaline phosphatase enzyme.

13. The method of claim 1, wherein the in vitro reaction is peroxidase label detection, wherein the entrapped reagent is an oxidase substrate, and wherein the substance capable of reacting with the entrapped reagent in the aqueous medium is a peroxidase enzyme.

14. The method of claim 1, wherein the in vitro reaction is a polymerase chain reaction (PCR), wherein the entrapped reagent is a PCR primer, wherein the substance capable of reacting with the entrapped reagent in the aqueous medium is a nucleic acid, and wherein the melting temperature of the wax bead is in the range from 50° C. to 100° C.

15. An in vitro reaction method comprising the steps of:
(a) adding a dispensable body containing a reagent to an aqueous medium containing a substance capable of reacting with said reagent, said dispensable body containing the reagent being prepared by entrapping an aqueous suspension of a reagent in a water insoluble and water impermeable wax bead having a melting temperature greater than 40° C., wherein the aqueous suspension of the reagent is entrappad in the water insoluble and water impermeable wax bead by injecting the aqueous suspension into essentially the center of a bead of molten wax and cooling the bead of molten wax with injected reagent therein to solidify the wax and form a bead of wax with the reagent entrapped within the bead; and
(b) heating the dispensable body containing the reagent to a temperature at which the wax bead melts and releases the entrapped reagent into the aqueous medium, wherein the reagent reacts with the substance in the aqueous medium.

16. The method of claim 15, wherein the entrapped reagent is a heat resistant enzyme.

17. The method of claim 15, wherein the entrapped reagent is an enzyme substrate.

18. The method of claim 15, wherein the entrapped reagent is a metal salt.

19. The method of claim 15, wherein the entrapped reagent is a labeling substance.

20. The method of claim 15, wherein the in vitro reaction is a polymerase chain reaction (PCR), wherein the entrapped reagent is a heat resistant DNA polymerase, and wherein the substance capable of reacting with the entrapped reagent in the aqueous medium is a nucleic acid.

21. The method of claim 15, wherein the in vitro reaction is a polymerase chain reaction (PCR), wherein the entrapped reagent is an enzyme substrate selected from the group consisting of nucleoside triphosphates (NTP's), deoxynucleoside triphosphates (dNTP's), and dideoxynucleoside triphosphates (ddNTP's), wherein the substance capable of reacting with the entrapped reagent in the aqueous medium is a polymerase enzyme, and wherein the melting temperature of the wax bead is in the range from 50° C. to 100° C.

22. The method of claim 15, wherein the in vitro reaction is a high temperature reverse transcriptase reaction (RTR), wherein the entrapped reagent is selected from reverse transcriptases, Tth DNA polymerase, and deoxynucleoside triphosphates (dNTP's), wherein the substance capable of reacting with the entrapped reagent in the aqueous medium is a nucleic acid, and wherein the melting temperature of the wax bead is about 70° C.

23. The method of claim 15, wherein the in vitro reaction is high temperature nucleic acid sequencing, wherein the entrapped reagent is selected from heat resistant enzymes and a labeling mixture of deoxynucleoside triphosphates (dNTP's), wherein the substance capable of reacting with the entrapped reagent in the aqueous medium is a nucleic acid, and wherein the melting temperature of the wax bead is higher than the temperature at which the template becomes fully denatured.

24. The method of claim 15, wherein the in vitro reaction is coupled high temperature reverse transcriptase reaction (RTR) and polymerase chain reaction (PCR), wherein entrapped reagent includes a chelating agent, MgCl$_2$, and forward and reverse PCR primers, wherein the substance capable of reacting with the entrapped reagent in the aqueous medium is a nucleic acid, and wherein the melting temperature of the wax bead is in the range from about 50° to about 100° C.

25. The method of claim 15, wherein the in vitro reaction is nucleic acid hybridization, wherein the entrapped reagent is an oligonucleotide, and wherein the substance capable of reacting with the entrapped reagent in the aqueous medium is a nucleic acid.

26. The method of claim 15, wherein the in vitro reaction is alkaline phosphatase label detection, wherein the entrapped reagent is a phosphorylated substrate, and wherein the substance capable of reacting with the entrapped reagent in the aqueous medium is an alkaline phosphatase enzyme.

27. The method of claim 15, wherein the in vitro reaction is peroxidase label detection, wherein the entrapped reagent is an oxidase substrate, and wherein the substance capable of reacting with the entrapped reagent in the aqueous medium is a peroxidase enzyme.

28. The method of claim 15, wherein the in vitro reaction is a polymerase chain reaction (PCR), wherein the entrapped reagent is a PCR primer, wherein the substance capable of reacting with the entrapped reagent in the aqueous medium is a nucleic acid, and wherein the melting temperature of the wax bead is in the range from 50° C. to 100° C.

* * * * *